United States Patent [19]

Röver

[11] Patent Number: 5,292,732
[45] Date of Patent: Mar. 8, 1994

[54] PYRROLOPYRAZINE DERIVATIVES

[75] Inventor: Stephan Röver, Grenzach-Wyhlen, Fed. Rep. of Germany

[73] Assignee: Hoffmann-La Roche Inc., Nutley, N.J.

[21] Appl. No.: 905,584

[22] Filed: Jun. 26, 1992

[30] Foreign Application Priority Data

Jul. 2, 1991 [CH] Switzerland .................. 1950/91
May 22, 1992 [CH] Switzerland .................. 1667/92

[51] Int. Cl.$^5$ .................. C07D 487/04; C07D 209/60; C07D 233/61; A61K 31/495
[52] U.S. Cl. .................. 514/249; 514/250; 544/343; 544/349; 548/449; 548/561; 549/458; 549/483
[58] Field of Search .................. 514/249, 250; 544/343, 544/349

[56] References Cited

U.S. PATENT DOCUMENTS

| | | | |
|---|---|---|---|
| 3,906,010 | 9/1975 | Pelosi, Jr. et al. | 260/347.5 |
| 3,931,247 | 1/1976 | Pelosi, Jr. | 260/347.2 |
| 4,188,389 | 2/1980 | Jirkovsky | 424/250 |

FOREIGN PATENT DOCUMENTS

| | | |
|---|---|---|
| 321431 | 12/1988 | European Pat. Off. |
| 1185080 | 12/1967 | United Kingdom |

OTHER PUBLICATIONS

Basanagoudar, Indian J Chem 30B, 1014 (1991).
Cernak, J. et al., Chemical Abstracts, vol. 94, abstract No. 54869z (1981).

(List continued on next page.)

*Primary Examiner*—Mark L. Berch
*Attorney, Agent, or Firm*—George M. Gould; George W. Johnston; John P. Parise

[57] ABSTRACT

The novel pyrrolopyrazines of the general formula

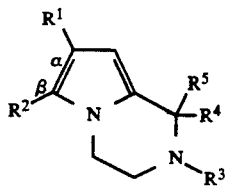

I wherein
one of $R^1$ and $R^2$ signifies aryl and the other signifies hydrogen, lower alkyl or aryl or $R^1$ and $R^2$ together with the two carbon atoms denoted by $\alpha$ and $\beta$ signify the group A;

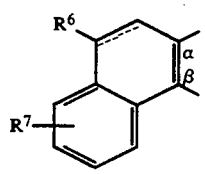

A $R^3$ signifies hydrogen or lower alkyl and $R^4$ signifies hydrogen or
$R^3$ and $R^4$ together signify an additional C/N bond;
$R^5$ signifies hydrogen or lower alkyl;
$R^6$ signifies hydrogen or lower alkyl;
$R^7$ signifies hydrogen, halogen, lower alkyl, optionally substituted lower alkoxy, or $C_{3-6}$-cycloalkyl, $C_{4-6}$-cycloalkenyl, $C_{3-6}$-cycloalkyloxy, hydroxy, trifluoromethanesulphonyloxy or optionally substituted benzyl-oxycarbonyloxy; and the dotted line signifies an optional additional C/C bond, and pharmaceutically acceptable acid addition salts of the compounds of formula I can be used in the control or prevention of illnesses or in the improvement of health, especially in the control or prevention of depressive states, cognitive disorders and neurodegenerative diseases such as Parkinson's disease and Alzheimer's disease.

13 Claims, No Drawings

OTHER PUBLICATIONS

Cernak, J., Chemical Abstracts, vol. 94, abstract No. 216535 (1981).
Itahara, Toshio, Journal of Organic Chemistry, vol. 50, pp. 5272–5275 (1985).
Janda, Lubomir et al., Chemical Abstracts, vol. 106, abstract No. 84385x (1987).
Obushak, N. D., et al., Chemical Abstracts, vol. 107, abstract No. 134142j (1987).
Baddar, F. G. et al., J. Chem. Soc. 1027–1032 (1959).
Buchi, G. et al., J. Org. Chem. 34, 1122 (1969).
Alexrod, J. A. et al., Biochem. Pharmac. 12, 1439–41 (1963).
Kruse, Heterocycles, 26, 3141 (1987).
Nahm, Steven et al., Tetrahedron Letters, 22, 3815 (1981).
Severin Th. et al., Chem. Ber. 108, 1756 (1975).
Pennanen, Seppo I., Heterocycles, 4, 1021 (1976).

PYRROLOPYRAZINE DERIVATIVES

FIELD OF THE INVENTION

The invention is concerned with pyrrolopyrazines and their use as inhibitors of monoamine oxidase enzymes.

SUMMARY OF THE INVENTION

The invention is concerned with compounds of the formula

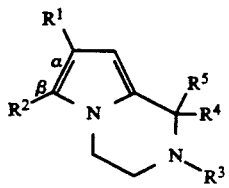

wherein
one of $R^1$ and $R^2$ signifies aryl and the other signifies hydrogen, lower alkyl or aryl, or $R^1$ and $R^2$ together with the two carbon atoms denoted by $\alpha$ and $\beta$ signify the group A;

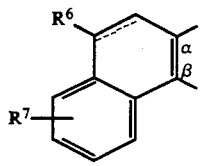

$R^3$ signifies hydrogen or lower alkyl and $R^4$ signifies hydrogen or
$R^3$ and $R^4$ together signify an additional C—N bond;
$R^5$ signifies hydrogen or lower alkyl;
$R^6$ signifies hydrogen or lower alkyl;
$R^7$ signifies hydrogen, halogen, lower alkyl, optionally substituted lower alkoxy, or $C_{3-6}$-cycloalkyl, $C_{4-6}$-cycloalkenyl, $C_{3-6}$-cycloalkyloxy, hydroxy, trifluoromethanesulphonyloxy or optionally substituted benzyloxycarbonyloxy; and
the ring carbon substituted by $R^6$ can either be saturated or unsaturated,
and pharmaceutically acceptable acid addition salts of the compounds of formula I.

It has surprisingly been found that the compounds of formula I have therapeutically valuable pharmacodynamic properties with low toxicity. The compounds of formula I and their pharmaceutically acceptable acid addition salts have monoamine oxidase (MAO) inhibiting properties. The compounds of formula I and their pharmaceutically acceptable acid addition salts are useful also in the control or prevention of depressive states, cognitive disorders and neurodegenerative diseases such as Parkinson's disease and Alzheimer's disease.

DETAILED DESCRIPTION OF THE INVENTION

The invention concerns compounds of the formula:

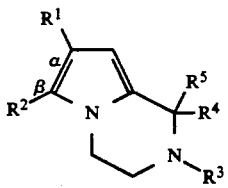

wherein
one of $R^1$ and $R^2$ is aryl and the other is hydrogen, lower alkyl or aryl, or $R^1$ and $R^2$ together with the two carbon atoms denoted by $\alpha$ and $\beta$, is the group A;

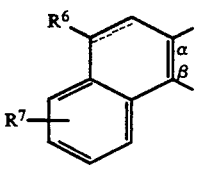

wherein:
$R^3$ is hydrogen or lower alkyl and $R^4$ is hydrogen or
$R^3$ and $R^4$ together are an additional C—N bond;
$R^5$ is hydrogen or lower alkyl;
$R^6$ is hydrogen or lower alkyl;
$R^7$ is hydrogen, halogen, lower alkyl, substituted or unsubstituted lower alkoxy, or $C_{3-6}$-cycloalkyl, $C_{4-6}$-cycloalkenyl, $C_{3-6}$-cycloalkyloxy, hydroxy, trifluoromethanesulphonyloxy or substituted or unsubstituted benzyloxycarbonyloxy; and
the ring carbon substituted $R^6$ either can be saturated or unsaturated,
and pharmaceutically acceptable acid addition salts of the compounds of formula I.

The term "lower" denotes residues and compounds having a maximum of twelve, preferably a maximum of eight, carbon atoms. The term "alkyl" denotes straight-chain or branched, saturated hydrocarbon residues such as, for example, methyl, ethyl, propyl, isopropyl, butyl or t-butyl. The term "alkoxy" denotes alkyl groups attached via an oxygen atom, such as, for example, methoxy, ethoxy, propoxy, isopropoxy, butoxy, tert.-butoxy or octyloxy. The term "optionally substituted alkoxy" means those alkoxy groups wherein one or more hydrogen atoms on the alkyl group can be replaced by hydroxy or a 5- or 6-membered saturated heterocycle which is attached via a nitrogen atom and which can contain an oxygen atom as a ring member, or the alkoxy can be substituted by an oxo group. The term "cycloalkyl" denotes cyclic saturated hydrocarbons such as, for example, cyclopropyl or cyclohexyl. The term "cycloalkenyl" denotes cyclic unsaturated hydrocarbons such as, for example, cyclohexenyl. The term "cycloalkyloxy" denotes a cyclic saturated hydrocarbon attached via an oxygen atom, such as, for example, cyclopentyloxy or cyclohexyloxy. The term "optionally substituted benzyloxycarbonyloxy" denotes benzyloxycarbonyloxy wherein a hydrogen atom on the phenyl ring can be replaced by e.g. a nitro group. Such substitutions include for example, 4-nitrobenzyloxycarbonyloxy. The term "halogen" denotes the forms F, Cl and Br.

The term "aryl" denotes phenyl, phenyl which is mono- or disubstituted by halogen, or a phenyl which is substituted by an optionally substituted lower alkoxy, lower alkyl, $C_{3-6}$-cycloalkyl, $C_{4-6}$-cycloalkenyl, hydroxy, trifluoromethyl, trifluoromethanesulphonyloxy, phenyl-lower-alkoxy, $C_{3-6}$-cycloalkyloxy or by optionally substituted benzyloxycarbonyloxy, or "aryl" is phenyl which is substituted by lower alkylenedioxy such as, for example, methylenedioxy or by bicycloalkyloxy such as, for example, 2-exonorbornyloxy.

The term "pharmaceutically acceptable acid addition salts" means salts formed with inorganic and organic acids such as hydrochloric acid, hydrobromic acid, nitric acid, sulphuric acid, phosphoric acid, citric acid, formic acid, fumaric acid, maleic acid, acetic acid, succinic acid, tartaric acid, methanesulphonic acid, p-toluenesulphonic acid, and the like. Such salts can be manufactured readily by any person skilled in the art having regard to the state of the art and taking into consideration the nature of the compound to be converted into a salt.

Preferred compounds of formula I are those in which $R^1$ and $R^2$ together are group A, especially those in which $R^7$ is $C_{3-6}$-cycloalkyl, $C_{3-6}$-cycloalkyloxy, halogen, lower alkoxy or lower alkyl.

Compounds in which $R^1$ is hydrogen and $R^2$ is aryl are also preferred.

Particularly preferred compounds are:
3,4-Dihydro-1-methyl-6-[p-(2-exonorbornyloxy)-phenyl]pyrrolo[1,2-a]pyrazine;
3-cyclopentyloxy-5,6,10,11-tetrahydro-8-methylbenzo[g]pyrazino[1,2-a]indole;
5,6,10,11-tetrahydro-3-isopropoxy-8-methylbenzo[g]pyrazino[1,2-a]indole;
3-n-butyl-5,6,10,11-tetrahydro-8-methylbenzo[g]pyrazino[1,2-a]indol;
3-cyclohexyl-5,6,10,11-tetrahydro-8-methylbenzo[g]pyrazino[1,2-a]indole; and
5,6,10,11-tetrahydro-3,8-dimethylbenzo[g]pyrazino[1,2-a]indole.

The compounds of formula I and their pharmaceutically acceptable acid addition salts can be prepared in accordance with the invention by a) cyclizing a compound of the formula

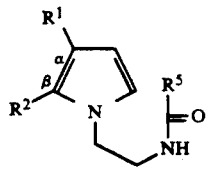

II wherein $R^1$, $R^2$ and $R^5$ have the above definitions, with the proviso that $R^1$ or $R^2$, or $R^1$ and $R^2$ together are not a group which is substituted by hydroxy or trifluoromethanesuphonyloxy or $C_{4-6}$-cycloalkenyl, or b) reacting a compound of the formula

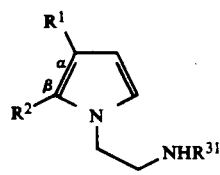

III wherein $R^1$ and $R^2$ have the above definitions and $R^{31}$ is hydrogen or lower alkyl, with the proviso that $R^1$ or $R^2$ or $R^1$ and $R^2$ together are not a group which is substituted by trifluoromethanesulphonyloxy or $C_{4-6}$-cycloalkenyl with an aldehyde of the formula $$R^5\text{---CHO} \qquad \text{IV}$$

wherein $R^5$ has the above definition, or c) reacting a compound of the formula

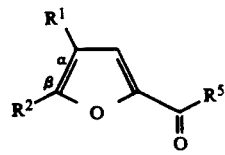

V wherein $R^1$, $R^2$ and $R^5$ have the above definitions, with 1,2-ethanediamine, or d) reducing a compound of the formula

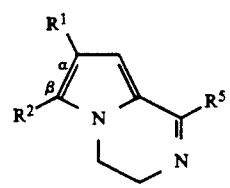

Ia or

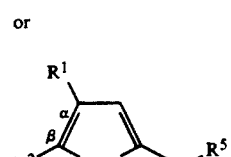

VI wherein $R^1$, $R^2$ and $R^5$ have the above definitions, $R^{32}$ is lower alkyl and X is halogen, or e) subjecting an alkoxy-substituted compound of formula I to an ether cleavage, or f) converting a compound of formula I in which $R^1$ and/or $R^2$ or $R^1$ and $R^2$ together represent a group which is substituted by phenolic hydroxy into a corresponding compound of formula I in which $R^1$ and/or $R^2$ or $R^1$ and $R^2$ together represent a group which is substituted by an optionally substituted alkoxy, by phenylalkyl-oxy, by $C_{3-6}$-cycloalkyloxy or by bicycloalkyloxy, or g) converting a compound of formula I in which $R^1$ and/or $R^2$ or $R^1$ and $R^2$ together represent a group which is substituted by phenolic hydroxy into a corresponding compound which is substituted by trifluoromethanesulphonyloxy, or h) converting a compound of formula I in which $R^1$ and/or $R^2$ or $R^1$ and $R^2$ are a group which is substituted by trifluoromethanesulphonyloxy into a corresponding compound which is substituted by lower alkyl, cyclopropyl or $C_{4-6}$-cycloalkenyl, or i) cleaving a compound of formula I which is substituted by an optionally substituted benzyloxycarbonyloxy, or j) hydrogenating a compound of formula I which is substituted by $C_{4-6}$-cycloalkylene, or k) converting a compound of formula I obtained by methods a)–j) above into a pharmaceutically acceptable acid addition salt.

Compounds of formula I in which $R^1$, $R^2$ and $R^5$ have the above definitions and where $R^3$ and $R^4$ together mean an additional C—N bond, with the proviso that $R^1$ or $R^2$ or $R^1$ and $R^2$ together do not represent a group which is substituted by hydroxy, trifluoromethanesulphonyloxy or $C_{4-6}$-cycloalkenyl can be prepared in accordance with process alternative a). This cyclization is preferably carried out by treatment with inorganic acid chlorides or acids, for example, with phosphorus oxychloride. The reaction temperature preferably lies in a temperature range of room temperature to the reflux temperature of the reaction mixture, with the reaction preferably being carried out at reflux temperature.

Compounds of formula I in which $R^1$, $R^2$ and $R^5$ have the above definitions, and where $R^3$ is hydrogen or lower alkyl with the proviso that $R^1$ or $R^2$ or $R^1$ and $R^2$ together are not a group which is substituted by trifluoromethanesulphonyloxy or $C_{4-6}$-cycloalkenyl and $R^4$ is hydrogen can likewise be manufactured in accordance with process alternative b). The reaction is preferably effected in a lower alcohol such as, for example, ethanol and the reaction is conveniently carried out at an elevated temperature, preferably at the reflux temperature of the reaction mixture.

Compounds of formula I in which $R^1$, $R^2$ and $R^5$ have the above definitions, and where $R^3$ and $R^4$ together are an additional C—N bond can be manufactured in accordance with process alternative c). This reaction is conveniently carried out at an elevated temperature, preferably at the reflux temperature of the reaction mixture. A 1,2-ethanediamine/water mixture in which the ratio is about 10:1 conveniently serves as the solvent and simultaneously as the reagent.

Compounds of formula I in which $R^1$, $R^2$ and $R^5$ have the above definitions, and where $R^3$ is hydrogen or lower alkyl, and $R^4$ is hydrogen can be manufactured in accordance with process alternative d). Sodium borohydride is preferably used for the reduction and a lower alcohol such as methanol or ethanol or a mixture of a lower alcohol with water, for example, a methanol-water mixture, is preferably used as the solvent. The reaction is carried out in a temperature range of about room temperature to the reflux temperature, with room temperature being preferred.

Compounds of formula I in which $R^1$ and/or $R^2$, or $R^1$ and $R^2$ together represent a group which is substituted by hydroxy, and where $R^3$, $R^4$ and $R^5$ have the above definitions can be manufactured in accordance with process alternative e). This reaction is carried out, for example, by treatment with hydrobromic acid. The reaction temperature preferably lies in a temperature range of about room temperature to the reflux temperature of the reaction mixture, with the reaction being preferably carried out at room temperature.

Compounds of formula I in which $R^1$ and/or $R^2$, or $R^1$ and $R^2$ together represent a group which is substituted by an optionally substituted alkoxy, by phenylalkyloxy, by $C_{3-6}$-cycloalkyloxy or by bicycloalkyloxy and $R^3$, $R^4$ and $R^5$ have the above definitions can be manufactured in accordance with process alternative f). The desired reaction can be performed by treating a compound of formula I in which $R^1$ and/or $R^2$, or $R^1$ and $R^2$ together represent a group which is substituted by phenolic hydroxy with a base such as, for example sodium hydroxide, in the presence of an alkylating agent. Suitable alkylating agents are, for example, methyl iodide, benzyl bromide, bromocyclopentane bicyclo[2,2,1]heptane bromide, 3-hydroxy-1-butyl toluenesulphonate, or the like. Suitable solvents are, for example, methylene chloride, dimethylformamide and the like. The reaction is preferably carried out in a temperature range of room temperature (about 23° C.) to the reflux temperature of the reaction mixture, with the reflux temperature being especially preferred.

Alternatively, the alkylation can also be carried out in the presence of triphenylphosphine and an azodicarboxylic acid ester such as, for example, diethyl azodicarboxylate using an alcohol as the alkylating agent in a inert solvent such as tetrahydrofuran at a temperature between −20° C. and the boiling temperature of the solvent. Moreover, the alkylation can also be carried out using an unsaturated compound such as isobutylene in an inert solvent such as methylene chloride in the presence of an acid such as trifluoromethanesulphonic acid. The reaction temperature is preferably −78° C. to −5° C.

Compounds of formula I in which $R^1$ and/or $R^2$, or $R^1$ and $R^2$ together represent a group which is substituted by trifluoromethanesulphonyloxy and in which $R^3$, $R^4$ and $R^5$ have the above definitions can be manufactured in accordance with process alternative g). The desired reaction can be carried out by reacting a compound of formula I in which $R^1$ and/or $R^2$, or $R^1$ and $R^2$ together signify a group which is substituted by phenolic hydroxy with a reactive trifluoromethanesulphonic acid derivative. The reaction is preferably carried out in an inert solvent such as e.g., dimethylacetamide, using a strong base such as e.g., sodium hydride, which generates the phenolate and reacting this with N-phenylbis(tri-fluoromethanesulphonimide). The reaction temperature lies between 0° C. and room temperature, preferably at 0° C.

Compounds of formula I in which $R^1$ and/or $R^2$, or $R^1$ and $R^2$ together represent a group which is substituted by lower alkyl, cyclopropyl or $C_{4-6}$-cycloalkenyl and in which $R^3$, $R^4$ and $R^5$ have the above definitions can be manufactured in accordance with process alternative h). The desired reaction can be carried out by reacting a compound of formula I in which $R^1$ and/or, $R^2$ or $R^1$ and $R^2$ together signify a group which is substituted by trifluoromethanesulphonyloxy with a corresponding metal-organic compound. The reaction is preferably carried out in an inert solvent such as dimethylformamide at an elevated temperature, preferably at 120° C., with the addition of a catalyst, preferably a palladium catalyst such as bis(triphenylphosphine)-palladium dichloride in the presence of co-catalysts such as triphenylphosphine and lithium chloride. Suitable metal-organic compounds are, for example, alkyltin compounds such as tetramethyltin, tetra-n-butyltin or tri-n-butyl-cyclo-propyl-tin and the like, or alkylcycloalkylene-tin compounds such as tri-n-butyl-1-cyclohexen-1-yl-tin or tri-n-butyl-2-cyclohexen-1-yl-tin.

Compounds of formula I in which $R^1$ and/or $R^2$, or $R^1$ and $R^2$ together represent a group which is substituted by phenolic hydroxy and in which $R^3$, $R^4$ and $R^5$ have the above definitions can be manufactured in accordance with process alternative i). The desired reaction can be carried out by hydrogenating a compound of formula I in which $R^1$ and/or $R^2$, or $R^1$ and $R^2$ together represent a group which is substituted by an optionally substituted benzyloxycarbonyloxy in an inert solvent such as ethyl acetate using a hydrogenation catalyst such as palladium-on-carbon at room temperature and normal pressure or by cleaving a compound of formula I in which $R^1$ and $R^2$ together represent a group which is substituted by 4-nitrobenzyloxycarbonyloxy in an inert solvent such as methylene chloride using an amine such as n-propylamine at room temperature.

Compounds of formula I in which $R^1$ and/or $R^2$, or $R^1$ and $R^2$ together represent a group which is substituted by $C_{4-6}$-cycloalkyl and in which $R^3$, $R^4$ and $R^5$ have the above definitions can be manufactured in accordance with process alternative j). The desired reaction can be carried out by hydrogenating a compound of formula I which is substituted by $C_{4-6}$-cycloalkenyl in an inert solvent such as methanol with the addition of an acid such as acetic acid or methanesulphonic acid using a hydrogenation catalyst such as palladium-on-carbon or tris(triphenylphosphine)rhodium(II) chloride, preferably at room temperature and normal pressure.

The compounds of formula I can be converted into pharmaceutically acceptable acid addition salts in accordance with process alternative k). Not only are salts with inorganic acids, but also salts with organic acids are suitable. Hydrochlorides, hydrobromides, nitrates, sulphates, phosphates, citrates, formiates, fumarates, maleates, acetates, succinates, tartrates, methanesulphonates, p-toluenesulphonates, and the like, are examples of such salts. These salts can be manufactured according to methods which are known per se and which are familiar to any person skilled in the art.

The various compounds which are used as starting materials can be prepared, for example, in accordance with the following Reaction Schemes and the subsequent descriptions of the various reactions.

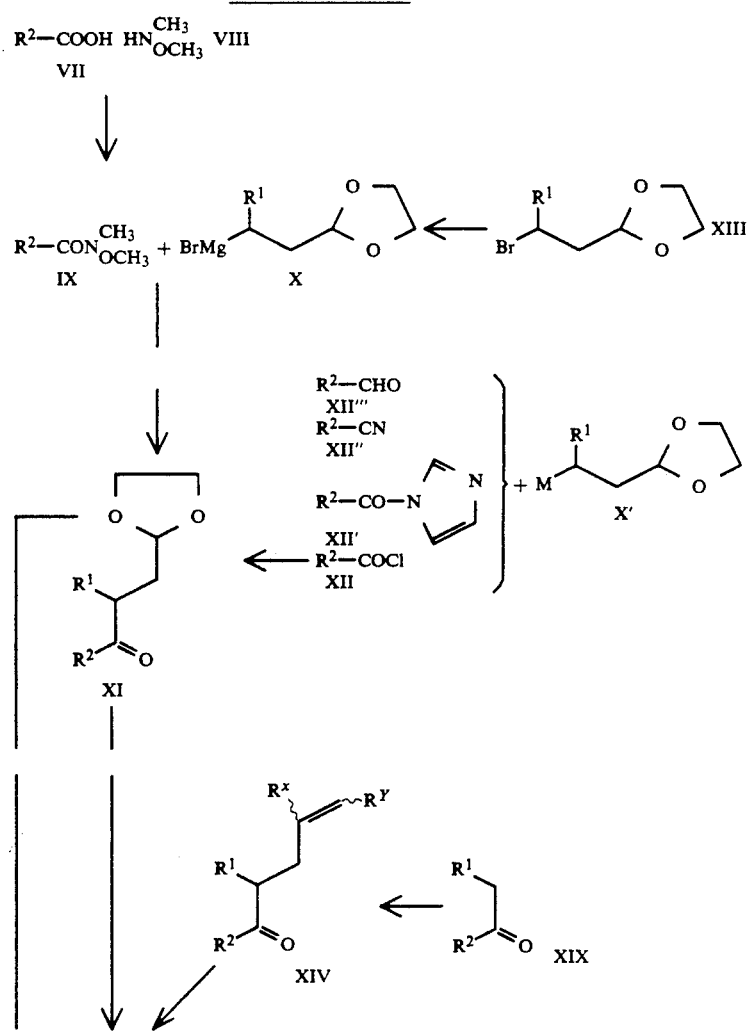

-continued
Reaction Scheme I

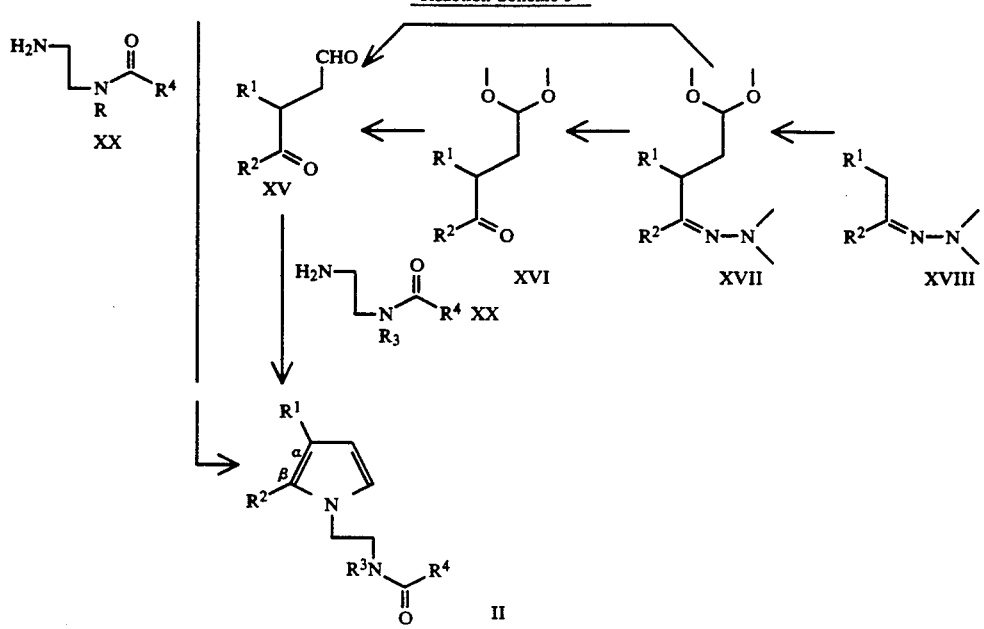

$R^1$, $R^2$ and $R^4$ have the definition given above, $R^3$ is lower alkyl or hydrogen, with the proviso that $R^1$ or $R^2$, or $R^1$ and $R^2$ together do not represent a group which is substituted by hydroxy, trifluoromethanesulphonyloxy or benzyloxycarbonyloxy, substituted benzyloxycarbonyloxy or $C_{4-6}$-cycloalkenyl. The N-methoxy-N-methylamide IX can be obtained by treating a carboxylic acid of formula VII with N,O-dimethyl-hydroxylamine (VIII) in the presence of a suitable condensation agent. Dicyclohexylcarbodiimide, 1,1-carbonyldiimidazole or the like are, for example, suitable condensation agents. The reaction can be effected in an inert solvent such as, for example, methylene chloride in a temperature range of room temperature to the boiling temperature, preferably at room temperature. The compounds of formula IX belong to a class of substances which are known per se. Such compounds are described, for example, in Tetrahedron Letters 22, 3815 (1981).

A compound of formula XI can be obtained by reacting a compound of formula IX with a compound of formula X. The compounds of formula X are accessible according to familiar methods from compounds of formula XIII. These compounds of formula XIII are known, see, for example, J. Org. Chem. 34, 1122 (1969) or can be prepared in an analogous manner.

The compounds of formula XI can, however, also be prepared by reacting a reactive carboxylic acid derivative such as a carboxylic acid chloride of formula XII, an imidazolide of formula XII' or a nitrile of formula XII'' with a metal-organic compound of type X' in a manner which is known in principle.

Likewise, the compunds of type XI can also be prepared in a manner which is known in principle by reacting an aldehyde of formula XII''' with a metal-organic compound of type X' and subsequently oxidizing the secondary alcohol in an inert solvent such as acetone using an oxidation agent such as manganese dioxide, preferably at the boiling temperature of the solvent.

Compounds of type XI in which $R^1$ is alkyl can be also obtained by alkylating compounds of type XI in which $R^1$ is hydrogen using alkylating reagents such as methyl iodide in an inert solvent such as tetrahydrofuran and in the presence of bases such as lithium diisopropylamine and complexing agents such as hexamethylphosphoric acid triamide.

A compound of formula XV can be obtained by hydrolyzing a compound of formula XI. This hydrolysis can be carried out in the presence of an acid, for example hydrochloric acid, in a pH range of about 0-2. This reaction is preferably carried out in a temperature range of about 0° C. to about 30° C. Tetrahydrofuran or the like can be used as the solvent.

Compounds of formula XV can also be prepared from compounds of formula XIV by ozonolysis and subsequent reductive working-up such as, for example, with dimethyl sulphide. This reaction can be carried out in solvents such as methanol, methylene chloride/methanol mixtures or the like. The compounds of formula XV belong to a class of substances which are known per se and are described, for example, in Chem. Ber. 108, 1756 (1975) and can also be prepared according to the method described there.

The compounds of formula XIV in which one of $R^x$ and $R^y$ is hydrogen and the other is hydrogen or lower alkyl are prepared by treating compounds of formula XIX with allyl alcohol or optionally alkyl-substituted allyl alcohols such as 3-hydroxy-1-butene in the presence of an acid catalyst such as, for example, p-toluenesulphonic acid and subsequent acid-catalyzed rearrangement according to known methods. This reaction is preferably carried out as a distillation with a catalyst such as p-toluenesulphonic acid and in solvents such as toluene or benzene in the presence of 2,2-dimethoxypropane.

Hydrazones of formula XVII can be obtained by converting a ketone of formula XIX according to methods known per se, into the hydrazones XVIII and alkylating compounds of formula XVIII. The alkylation can be carried out in the presence of a strong base, for example n-butyllithium, and using bromoacetaldehyde dimethyl acetal as the alkylating agent. Tetrahydrofuran is preferably used as the solvent. The reaction is preferably carried out in a temperature range of about −30° C. to room temperature.

Compounds of formula XVI can be obtained by hydrolyzing compounds of formula XVII. This reaction can be carried out under oxidizing conditions, for example in the presence of a periodate, in an inert solvent such as tetrahydrofuran or like solvents in the presence of water in a temperature range of about 20°–50° C. The compounds of formulae XV, XVI, XVII and XVIII belong to classes of substances which are known per se. Such compounds are described, for example, in Heterocycles 26, 3141 (1987).

The ketones of formula XIX are known, see, for example, J. Chem. Soc. 1027–1031, 1959, or can be prepared according to analogous methods.

Compounds of formula XVII can also be converted into ketones of formula XVI with transition metal salts, for example copper(II) chloride, in solvents such as tetrahydrofuran/water mixtures and the like. This reaction is preferably carried out in a temperature range of room temperature to the boiling temperature of the mixture, with room temperature being especially preferred.

Compounds of formula XV can be obtained by hydrolyzing compounds of formula XVI. The hydrolysis can be carried out in solvents such as methylene chloride and in the presence of oxalic acid/water.

Compounds of formula XV can also be obtained directly by hydrolysis from compounds of formula XVII. This hydrolysis can be carried out in the presence of an acid, for example hydrochloric acid, in a pH range of about 0–2. This reaction is preferably carried out in a temperature of about 0° to about 30° C. Tetrahydrofuran or the like can be used as the solvent.

The desired compound II can be obtained by treating a compound of formula XV with an amide of formula XX. This reaction is carried out in the presence of an acid, for example acetic acid, or in an inert solvent such as, for example, methylene chloride in the presence of molecular sieve. The reaction is preferably carried out at room temperature up to the boiling temperature of the reaction mixture.

The desired compound II can also be obtained by reacting a compound of formula XI with an amide of formula XX. This reaction can be carried out in the presence of acetic acid. It is preferably carried out at the reflux temperature of the reaction mixture.

Reaction Scheme II

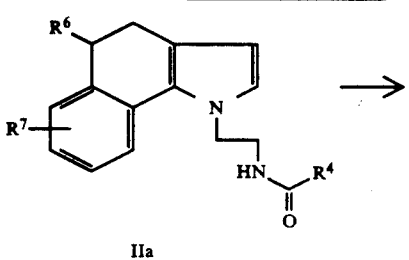

IIa

-continued
Reaction Scheme II

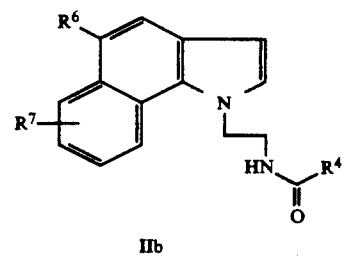

IIb $R^4$, $R^6$ and $R^7$ have the definitions given above.

A compound of formula $II_b$ can be obtained by treating a compound of formula $II_a$ with a dehydrogenating agent, for example 2,3-dichloro-5,6-dicyano-1,4-benzoquinone in an inert solvent such as, for example, toluene. The reaction is preferably carried out at the boiling temperature of the mixture. Compounds of formula $II_a$ i.e. compounds of formula II in which $R^1$ and $R^2$ together signify the group A, but saturated can be obtained according to Reaction Scheme I or the like.

Reaction Scheme III

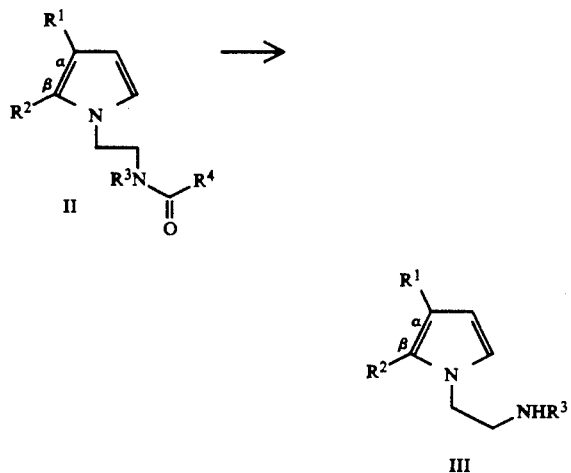

III

A compound of formula III can be obtained by treating a compound of formula II with an alkali metal hydroxide, e.g. potassium hydroxide, in an alcohol such as, for example, ethylene glycol and in the presence of water. This reaction is preferably carried out at an elevated temperature, especially in a temperature range of about 100° C. to about 120° C. The compounds of formula II can be prepared in accordance with Reaction Scheme I or the like.

Reaction Scheme IV

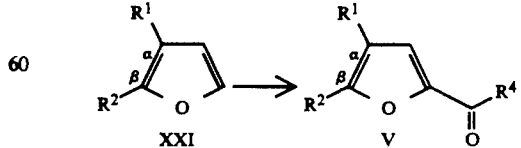

XXI            V

The compounds of formula V which are used as starting materials can be prepared starting from compounds of general formula XXI in which $R^1$, $R^2$ and $R^4$ have the above significance according to methods which are known per se; see, for example, Heterocycles 4, 1021 (1976).

Compounds of formula XXIa in which $R^2$ is methyl can be prepared starting from compounds of formula XXIb in which $R^2$ is hydrogen by bromination, bromine-lithium exchange and alkylation with methyl iodide. The bromination is preferably carried out in an inert solvent such as diethyl ether or tetra- hydrofuran at room temperature using a brominating agent such as N-bromosuccinimide. The bromine-lithium exchange is preferably carried out in the aforementioned solvents at a low temperature, preferably at $-78°$ C., using a lithium-alkyl compound such as n-butyllithium in the presence of a complexing agent such as N,N,N',N'-tetramethylethylenediamine and the methylation is then advantageously achieved by the addition of methylating reagents such as methyl iodide to the reaction solution at a low temperature, preferably between $-50°$ and $-20°$ C.

Reaction Scheme V

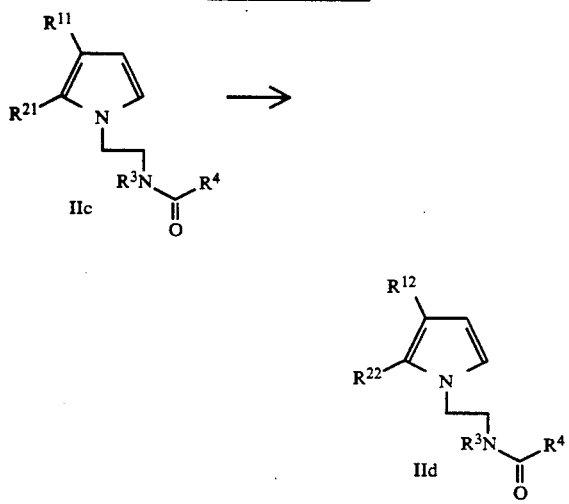

Compounds of formula IId in which $R^{12}$ or $R^{22}$ or $R^{12}$ and $R^{22}$ together are a group which is substituted by hydroxy and $R^3$ and $R^4$ have the definitions given above can be prepared by subjecting a compound of formula IIc in which $R^{11}$ or $R^{21}$, or $R^{11}$ and $R^{21}$ together carry an alkoxy substituent, to an ether cleavage. The ether cleavage is preferably carried out in an inert solvent such as methylene chloride using a Lewis acid such as boron tribromide at a low temperature, preferably at about $-15°$ C. to about room temperature.

Reaction Scheme VI

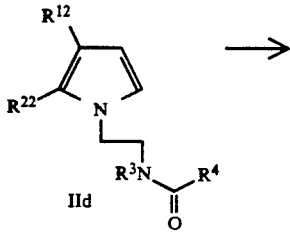

-continued
Reaction Scheme VI

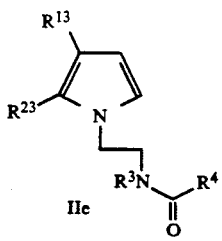

Compounds of formula IIe in which $R^{13}$ or $R^{23}$, or $R^{13}$ and $R^{23}$ together carry a carbonate or a substituted carbonate as a substituent, and in which $R^3$ and $R^4$ have the definitions given above can be prepared by esterifying compounds of formula IId in which $R^{12}$ or $R^{22}$, or $R^{12}$ and $R^{22}$ together carry a hydroxy substituent. The esterification is preferably carried out in inert solvents such as dioxane/water mixtures using a reactive carbonic acid derivative such as benzyl chloroformate or 4-nitrobenzyl chloroformate in the presence of a base such as sodium hydrogen carbonate at temperatures between room temperature and the boiling temperature of the solvent, preferably at room temperature.

The compounds of formulae II, III, V and VI which are used as intermediates are novel and are also an aspect of the invention. The remaining compounds which are used as starting materials or intermediates belong to classes of substances which are known per se.

The compounds of formula I and their pharmaceutically usable acid addition salts have monoamine oxidase (MAO) inhibiting activity. On the basis of this activity, the compounds of formula I and their pharmaceutically usable acid addition salts can be used for the treatment of depressive states, cognitive disorders and neurodegenerative diseases such as Parkinson's disease and Alzheimer's disease.

The MAO inhibiting activity of the compounds in accordance with the invention can be determined in vitro or ex vivo using standard methods. The preparations to be tested were investigated in the tests described hereinafter, which were based on the methods of R. J. Wurtmann and J. A. Axelrod [Biochem. Pharmac. 12, 1439–41 (1963).

in vitro:

Isolated rat brains are homogenized in 0.1 molar potassium phosphate buffer (pH 7.4) in the ratio 1:4 (weight/volume), the homogenate is diluted with the same buffer in the ratio 1:5 (volume/volume) and stored at $-20°$ C. A mixture of the following composition was used for the incubation:

100 μl of 1M phosphate buffer (pH 6.7);
100 μl of solution of the substance to be tested in water or in 10% aqueous dimethyl sulphoxide;
20 μl of rat brain homogenate; and as the substrate
80 μl of $^{14}$C-labelled serotonin (5-HT) or $^{14}$C-labelled phenylethylamine (PEA), the radioactive concentration of which amounts to 100,000 decay per minute and which is used in a final concentration of $2\times10^{-4}$M and, respectively, $2\times10^{-5}$M.

A pre-incubation at $37°$ C. is effected for 30 minutes prior to the addition of the substrate. The incubation (in the presence of the substrate) is likewise effected at $37°$ C. and lasts for 10 minutes. The reaction is stopped by the addition of 200 μl of 2N hydrochloric acid.

In order to extract the desaminated product, the mixture is shaken for 10 minutes with 5 ml of diethyl ether or with 5 ml of n-heptane depending on whether 5-HT or PEA is used as the substrate, whereupon the mixture is centrifuged, the aqueous phase is frozen in a dry-ice bath, the organic phase is transferred into a counting glass and the radioactive concentration is determined in a β-counter.

The activity of the MAO in comparison to the control homogenates (without substance to be tested) is obtained on the basis of the β-values and the $IC_{50}$ is defined as that concentration of a substance to be tested which reduces the activity of the MAO upon the substrate 5-HT or PEA by 50%.

The thus-determined activity of some compounds in accordance with the invention will be evident from the $IC_{50}$ values set forth in the Table I:

TABLE I

| Compound | $IC_{50}$ μM | |
|---|---|---|
| | 5HT | PEA |
| 3,4-Dihydro-1-methyl-6-phenylpyrrolo[1,2-a]pyrazine | 0.3 | >>1 |
| 6-(p-Chlorophenyl)-3,4-dihydro-1-methylpyrrolo-1,2-a]pyrazine | 0.35 | 10 |
| 3,4-Dihydro-6-(p-methoxyphenyl)-1-methyl-pyrrolo[1,2-a]pyrazine | 0.05 | >1 |
| 5,6,10,11-Tetrahydro-8-methylbenzo[g]pyrazino-[1,2-a]indole | 0.03 | >1 |
| 5,6,8,9,10,11-Hexahydro-8-methylbenzo[g]pyrazino[1,2-a]indole | 0.09 | >1 |
| 3,4-Dihydro-1-methyl-7-phenylpyrrolo[1,2-a]pyrazine | 0.09 | >>1 |
| 6-[p-(Cyclopentyloxy)phenyl]-3,4-dihydro-1-methylpyrrolo-[1,2,-a]pyrazine | 0.01 | <0.001 |
| 3,4-Dihydro-1-methyl-6-[p-(2-exonorbornyloxy)-phenyl]pyrrolo[1,2-a]pyrazine | 0.02 | 0.003 |
| 3-Chloro-5,6,10,11-tetrahydro-8-methylbenzo[g]-pyrazino[1,2-a]indole | 0.01 | >>1 |
| 5,6,10,11-Tetrahydro-3-methoxy-8-methyl-benzo-[g]pyrazino[1,2-a]indole | 0.0008 | >1 |
| 5,6,10,11-Tetrahydro-3-isopropoxy-8-methyl-benzo[g]pyrazino[1,2-a]indole | 0.0004 | 0.014 |
| 3-Cyclopentyloxy-5,6,10,11-tetrahydro-8-methyl-benzo[g]pyrazino[1,2-a]indole | 0.001 | 0.007 |
| 5,6,10,11-Tetrahydro-3,8-dimethyl-benzo[g]pyrazino[1,2-a]indole | 0.002 | >1 |
| 3-Cyclohexyl-5,6,10,11-tetrahydro-8-methyl-benzo[g]pyrazino[1,2,-a]indole | 0.002 | 0.16 | ex vivo:

The compounds to be tested are investigated for the inhibition of MAO in the brain and liver of male albino rats (Fü-SPF, 100–140 g. The test compounds are administered orally as a solution or suspension in water in a dosage of 100 μmol per kilogram body weight. After 2 hrs. the animals are narcotized and decapitated. The brain (without cerebellum) and a portion of the liver are dissected out and submitted analogously to the above-described procedure for the determination of the MAO inhibiting activity, whereby the amount of enzyme used is 20 μl of a 1:20 homogenate in the case of brain and 20 μl of a 1:80 homogenate in the case of liver. The activity of the compounds is determined from a comparison of the β-values with the values for control animals treated with vehicle and is given in percentage of the control values.

The thus-determined activity of some compounds in accordance with the invention will be evident from the values set forth in Table II:

TABLE II

| Compound | MAO inhibition | | | |
|---|---|---|---|---|
| | Brain | | Liver | |
| | 5HT | PEA | 5HT | PEA |
| 5,6,10,11-Tetrahydro-8-methylbenzo[g]-pyrazino[1,2-a]indole | 48% | 87% | 47% | 81% |
| 5,6,8,9,10,11-Hexahydro-8-methylbenzo-[g]pyrazino[1,2-a]indole | 69% | 95% | 55% | 78% |
| 6-[p-(Cyclopentyloxy)phenyl]-3,4-dihydro-1methylpyrrolo-[1,2-a]pyrazine | 67% | 33% | 38% | 56% |
| 3-Chloro-5,6,10,11-tetrahydro-8-methylbenzo[g]pyrazino-[1,2-a]indole | 42% | 93% | 20% | 96% |
| 3,4-Dihydro-1-methyl-6-[p-(2-exonor-bornyloxy)phenyl]pyrrolo[1,2-a]pyrazine | 45% | 11% | 51% | 10% |
| 5,6,10,11-Tetrahydro-3-methoxy-8-methylbenzo[g]pyrazino[1,2-a]indole | 28% | 86% | 5% | 87% |
| 5,6,10,11-Tetrahydro-3-isopropoxy-8-methylbenzo[g]pyrazino[1,2-a]indole | 8% | 60% | 10% | 75% |
| 3-Cyclopentyloxy-5,6,10,11-tetrahydro-8-methylbenzo[g]pyrazino[1,2-a]indole | 13% | 45% | 8% | 50% |
| 5,6,10,11-Tetrahydro-3,8-dimethyl-benzo[g]pyrazino[1,2-a]indole | 43% | 82% | 17% | 96% |

The toxicity of the compounds in accordance with the invention is investigated by orally administering different dosages of the dissolved or suspended compounds to mice. One mouse is used per dosage. The dosage is halved stepwise so that a dosage range of about 1.5 to the power of ten is covered. The results of this preliminary toxicity testing are reproduced in the form of two administered dosages.

The higher dosage (LLD=lowest lethal dose) led to death within 24 hrs., the lower dosage (HTD=highest tolerated dose) was survival. (Dosage data in miligram per kilogram body weight, administered orally).

TABLE III

| Compound | HTD | LLD |
|---|---|---|
| 3,4-Dihydro-1-methyl-6-phenylpyrrolo[1,2-a]pyrazine fumarate (1:1) | 312 | 625 |
| 6-(p-Chlorophenyl-3,4-dihydro-1-methylpyrrolo-[1,2-a]pyrazine fumarate (1:1) | 312 | 625 |
| 5,6,10,11-Tetrahydro-8-methylbenzo[g]pyrazino-[1,2-a]indole fumarate (2:3) | 156 | 312 |
| 5,6,8,9,10,11-Hexahydro-8-methylbenzo[g]pyrazino[1,2-a]indole fumarate (1:1) | 312 | 625 |
| 6-[p-(Cyclopentyloxy)phenyl]-3,4-dihydro-1-methylpyrrolo[1,2-a]pyrazine fumarate (1:1) | 312 | 625 |
| 3-Chloro-5,6,10,11-tetrahydro-8-methylbenzo-[g]pyrazino[1,2-a]indole fumarate (1:1) | 125 | 250 |
| 3-Chloro-5,6,8,9,10,11-hexahydro-8-methyl-benzo[g]pyrazino[1,2-a]indole fumarate (1:1) | 500 | 1000 |
| 3-Cyclopentyloxy-5,6,10,11-tetrahydro-8-methylbenzo[g]pyrazino[1,2-a]indole fumarate (1:1) | 250 | 500 |

The compounds of formula I and the pharmaceutically acceptable acid addition salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

For the manufacture of pharmaceutical preparations, the products in accordance with the invention can be processed with pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerol, vegetable oils and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances. Medicaments containing a product in accordance with the invention and a therapeutically inert carrier as well as a process for their manufacture, which comprises bringing a product in accordance with the invention and, if desired, one or more other therapeutically valuable substances into a galenical administration form, are also objects of the present invention.

In accordance with the invention compounds of formula I as well as their pharmaceutically acceptable acid addition salts can be used in the control or prevention of depressive states, cognitive disorders and neurodegenerative diseases such as Parkinson's disease and Alzheimer's disease. The dosage can vary within wide limits and will, of course, be fitted to the individual requirements in each particular case. In the case of oral administration the daily dosage lies in a range of about 50–500 mg of a compound of formula I, although the upper limit can also be exceeded should this be shown to be indicated.

The following Examples serve to illustrate the present invention in more detail. They are, however, not intended to limit its scope in any manner. Unless indicated otherwise, the Examples were carried out as written.

EXAMPLE 1 a) 2-(2-Bromoethyl)-1,3-dioxolane (40 ml) was added dropwise within 15 minutes under argon and while stirring at a maximum 30° C. to a suspension of Rieke magnesium, prepared from 44.9 g of magnesium chloride, in 1500 ml of absolute tetrahydrofuran. The suspension was stirred at room temperature (about 23° C.) for 15 minutes, cooled to 0° C. and, after the addition of 43.5 g of copper(I) bromide, stirred at 5° C. for 15 minutes. After cooling to −70° C. 33 ml of 3-chlorobenzoyl chloride were added dropwise within 10 minutes. The reaction mixture was stirred at −70° C. for 15 minutes and at room temperature for 2 hours and subsequently hydrolyzed with 1000 ml of saturated ammonium chloride solution while cooling at a maximum 20° C. After the addition of 500 ml of water the mixture was extracted three times with 1000 ml of ethyl acetate each time. The combined organic extracts were washed with 1000 ml of saturated sodium chloride solution, dried over MgSO$_4$ and freed from solvent. 59.2 g of oil were chromatographed on 1500 g of silica gel with ethyl acetate/hexane (1:3) as the eluent. 20.9 g (34%) of 3'-chloro-3-(1,3-dioxolan-2-yl)propiophenone were isolated as a yellow oil.

b) 3'-Chloro-3-(1,3-dioxolan-2-yl)propiophenone (10.0 g) dissolved in 90 ml of tetrahydrofuran was treated with 180 ml of 2N hydrochloric acid solution at room temperature while stirring and under argon and the mixture was stirred at room temperature overnight. The reaction mixture was extracted once with 200 ml of methylene chloride and twice with 100 ml of methylene chloride each time. The organic extracts were combined, dried with MgSO$_4$ and freed from solvent. The residue, 8.2 g of yellow oil, was dissolved in 20 ml of acetic acid without further purification and added under argon and while stirring to a solution of 8.5 g of N-acetylethylenediamine in 50 ml of acetic acid. The reaction solution was stirred at room temperature for 2½ hours, the acetic acid was subsequently removed in a vacuum. The residue was taken up in 200 ml of methylene chloride and washed with a mixture of 100 ml of saturated sodium hydrogen carbonate solution and 60 ml of 2N sodium hydroxide solution. The aqueous phase was back-extracted three times with 100 ml of methylene chloride each time. The organic phases were combined, dried with MgSO$_4$ and freed from solvent. The residue, 10.2 g of brown oil, was chromatographed on 500 g of silica gel with ethyl acetate/hexane (2:1) as the eluent. 3.5 g (32%) of N-[2-[2-(m-chlorophenyl)-pyrrol-1-yl]ethyl]acetamide were isolated as a yellow-brown oil. MS: m/e=262 (M+).

c) N-[2-[2-(m-Chlorophenyl)-pyrrol-1-yl]ethyl]acetamide (3.5 g) was treated with 15 ml of phosphorus oxychloride under argon and boiled for 1 hour while stirring. The reaction mixture was hydrolyzed at 0° C. with 100 ml of 2N sodium hydroxide solution and 50 ml of 28% sodium hydroxide solution, diluted with 1000 ml of water and extracted with diethyl ether (1×200 ml, 2×100 ml). The organic extracts were combined, washed once with 100 ml of water, dried over MgSO$_4$ and freed from solvent. 1.0 g of a total of 3.0 g of crude product were dissolved in a 25-fold amount of ethanol and treated with 1.1 equivalents of a saturated solution of fumaric acid in ethanol. After the addition of 30 ml of ethyl acetate there crystallized 1.2 g (75%) of 6-(m-chlorophenyl)-3,4-dihydro-1-methylpyrrolo[1,2-a]pyrazine fumarate (1:1); m.pt.: 158°–160° C. (dec.).

EXAMPLE 2 a) 2-(2-Bromoethyl)-1,3-dioxolane (40 ml) was added dropwise within 15 minutes under argon and while stirring at a maximum 30° C. to a suspension of Rieke magnesium, prepared from 45.0 g of magnesium chloride, in 1500 ml of absolute tetrahydrofuran. The suspension was stirred at room temperature for 15 minutes, cooled to 0° C. and, after the addition of 43.5 g of copper(I) bromide, stirred at 5° C. for 15 minutes. After cooling to −70° C., 33 ml of 4-chlorobenzoyl chloride was added dropwise within 10 minutes. The reaction mixture was stirred at −70° C. for 15 minutes and at room temperature for 2 hours and subsequently hydrolyzed with 1000 ml of saturated ammonium chloride solution while cooling at a maximum 20° C. After the addition of 500 ml of water the mixture was extracted three times with 1000 ml of ethyl acetate each time. The combined organic extracts were washed with 1000 ml of saturated sodium chloride solution, dried over MgSO$_4$ and freed from solvent. 63.0 g of residue were chromatographed on 2000 g of silica gel with ethyl acetate/hexane (1:1) as the eluent. 36.5 g (59%) of 4'-chloro-3(1,3-dioxolan-2-yl)propiophenone were isolated as a yellow, amorphous solid.

b) 4'-Chloro-3-(1,3-dioxolan-2-yl)propiophenone (10.0 g) dissolved in 100 ml of tetrahydrofuran was treated with 180 ml of 2N hydrochloric acid solution at room temperature while stirring and under argon and the mixture was stirred at room temperature for 5 hours. The reaction mixture was extracted once with 250 ml of methylene chloride and twice with 100 ml of methylene chloride each time. The organic extracts were combined, dried with MgSO$_4$ and freed from solvent. The residue, 8.1 g of brown oil, was dissolved in 30 ml of acetic acid without further purification and added under argon and while stirring to a solution of 10.0 g of N-acetylethylenediamine in 60 ml of acetic acid. The reaction solution was stirred at room temperature for 3 hours, the acetic acid was subsequently removed in a vacuum. The residue was taken up in 150 ml of methylene chloride and washed with a mixture of 100 ml of saturated sodium hydrogen carbonate solution and 200 ml of 2N sodium hydroxide solution. The aqueous phase was back-extracted three times with 100 ml of methylene chloride each time. The organic phases were combined, dried with MgSO$_4$ and freed from solvent. The residue, 9.5 g of brown, amorphous material, was chromatographed on 500 g of silica gel with ethyl acetate/hexane (2:1) as the eluent. 2.2 g (20%) of N-[2-[2-(p-chlorophenyl)-pyrrol-1-yl]ethyl]acetamide were isolated as a brown oil. MS: m/e=262 (M+).

c) N-[2-[2-(p-Chlorophenyl)-pyrrol-1-yl]ethyl]acetamide (2.2 g) was treated with 10 ml of phosphorus oxychloride under argon and boiled for 45 minutes while stirring. The reaction mixture was hydrolyzed at 0° C. with 300 ml of 2N sodium hydroxide solution, diluted with 500 ml of water and extracted three times with 100 ml of methylene chloride. The organic extracts were combined, dried with MgSO$_4$ and freed from solvent. 0.9 g of a total of 1.9 g of crude product was dissolved in a 30-fold amount of ethanol and treated with 1.1 equivalents of a saturated solution of fumaric acid in ethanol. After the addition of 25 ml of ethyl acetate there crystallized 0.9 g (64%) of 6-(p-chloro-phenyl)-3,4-dihydro-1-methylpyrrolo[1,2-a]pyrazine fumarate (1:1); m.pt.: 187°-189° C. (dec.).

EXAMPLE 3 a) 2-(2-Bromoethyl)-1,3-dioxolane (45 ml) was added dropwise within 15 minutes under argon and while stirring at a maximum 30° C. to a suspension of Rieke magnesium, prepared from 51.2 g of magnesium chloride, in 1300 ml of absolute tetrahydrofuran. The suspension was stirred at room temperature for 15 minutes, cooled to 0° C. and, after the addition of 49.6 g of copper(I) bromide, stirred at 5° C. for 15 minutes. After cooling to −70° C. 50.0 g of p-anisoyl chloride dissolved in 150 ml of absolute tetrahydrofuran were added dropwise within 20 minutes. The reaction mixture was stirred at −70° C. for 30 minutes and at room temperature for 2 hours and subsequently hydrolyzed with 800 ml of saturated ammonium chloride solution while cooling at a maximum 30° C. After the addition of 500 ml of water the mixture was extracted three times with 700 ml of ethyl acetate each time. The combined organic extracts were washed with 1000 ml of saturated sodium chloride solution, dried over MgSO$_4$ and freed from solvent. 82.4 g of dark brown oil were chromatographed on 2000 g of silica gel with ethyl acetate/hexane (1:1) as the eluent. 48.8 g (71%) of 3-(1,3-dioxolan-2-yl)-4'-methoxypropiophenone were isolated as a yellow-orange oil.

b) 3-(1,3-Dioxolan-2-yl)-4'-methoxypropiophenone (38.8 g) was dissolved in 100 ml of acetic acid and added under argon and while stirring to a solution of 33.5 g of N-acetylethylene-diamine in 500 ml of acetic acid. The reaction solution was heated to reflux overnight, the acetic acid was subsequently removed in a vacuum. The residue was taken up in 500 ml of methylene chloride and washed with a mixture of 200 ml of saturated sodium hydrogen carbonate solution and 400 ml of 2N sodium hydroxide solution. The aqueous phase was extracted three times with 100 ml of methylene chloride each time, the organic phases were combined, dried with MgSO$_4$ and freed from solvent. The residue, 49.6 g of brown oil, was chromatographed on 500 g of silica gel with ethyl acetate as the eluent. 27.8 g (66%) of N-[2-[2-(p-methoxyphenyl)-pyrrol-1-yl]ethyl]acetamide were isolated as a yellow-brown oil. MS: m/e=258 (M+).

c) N-[2-[2-(p-Methoxyphenyl)-pyrrol-1-yl]ethyl]acetamide (2.1 g) was treated with 10 ml of phosphorus oxychloride under argon and boiled for ¼ hour while stirring. The reaction mixture was hydrolyzed at 0° C. with 100 ml of 2N sodium hydroxide solution and 50 ml of 28% sodium hydroxide solution, diluted with 600 ml of water and extracted three times with 100 ml of methylene chloride each time. The organic extracts were combined, dried with MgSO$_4$ and freed from solvent. 1.0 g of a total of 2.0 g of crude product was dissolved in a 40-fold amount of ethanol and treated with 1.1 equivalents of a saturated solution of fumaric acid in ethanol. There was obtained 0.6 g (42%) of 3,4-dihydro-6-(p-methoxyphenyl)-1-methyl-pyrrolo[1,2-a]pyrazine fumarate (1:1); m.pt.: 167°-169° C. (dec.).

EXAMPLE 4 a) 3-(1,3-Dioxolan-2-yl)-4'-(trifluoromethyl)-propiophenone (6.4 g) was added under argon and while stirring to a solution of 4.8 g of N-acetylethylenediamine in 70 ml of acetic acid. The reaction mixture was refluxed overnight, the acetic acid was subsequently removed in a vacuum. The residue was taken up in 200 ml of methylene chloride and washed with a mixture of 100 ml of saturated sodium hydrogen carbonate solution and 70 ml of 2N sodium hydroxide solution. The aqueous phase was back-extracted twice with 100 ml of methylene chloride each time, the organic phases were combined, dried with MgSO$_4$ and freed from solvent. The residue, 9.4 g of yellow-brown solid was chromatographed on 500 g of silica gel with ethyl acetate as the eluent. 5.4 g (78%) of N-[2-[2-[4-(trifluoromethyl)-phenyl]-pyrrol-1-yl]ethyl]acetamide were isolated as a yellow amorphous solid. MS: m/e=296 (M+).

b) N-[2-[2-[4-(Trifluoromethyl)phenyl]-pyrrol-1-yl]ethyl]acetamide (5.4 g) was treated with 25 ml of phosphorus oxychloride under argon and boiled for 1 hour while stirring. The reaction mixture was hydrolyzed at 0° C. with 100 ml of 2N sodium hydroxide solution and 150 ml of 28% sodium hydroxide methylene chloride (1×300 ml, 2×100 ml). The organic extracts were combined, dried with MgSO$_4$ and freed from solvent. 2.5 g of a total of 5.0 g of crude product was dissolved in a 30-fold amount of ethanol and treated with 1.1 equivalents of a saturated solution of fumaric acid in ethanol. There was obtained 2.7 g (76%) of 3,4-dihydro-1-methyl-6-[4-(trifluoro-methyl)phenyl]pyrrolo[1,2-a]pyrazine fumarate (1:1); m.pt.: 165°-167° C. (dec.).

EXAMPLE 5 a) 2-(2-Bromoethyl)-1,3-dioxolane (32.7 ml) was added dropwise within 15 minutes under argon and while stirring at a maximum 30° C. to a suspension of Rieke magnesium, prepared from 37.5 g of magnesium chloride, in 1200 ml of absolute tetrahydrofuran. The suspension was stirred at room temperature for 15 minutes, cooled to 0° C. and, after the addition of 36.4 g of copper(I) bromide, stirred at 0° C. for 15 minutes. After cooling to −70° C. 45.0 g of 3,4-dichlorobenzoyl chloride dissolved in 100 ml of absolute tetrahydrofuran were added dropwise within 20 minutes. The reaction mixture was stirred at −70° C. for 30 minutes and at room temperature for 2 hours and subsequently hydrolyzed with 800 ml of saturated ammonium chloride solution while cooling at a maximum 20° C. After the addition of 500 ml of water the mixture was extracted three times with ethyl acetate (1×800 ml, 2×500 ml). The combined organic extracts were dried over $MgSO_4$ and freed from solvent. The residue, 65.0 g of brown oil, was chromatographed on 1500 g of silica gel with ethyl acetate/hexane (1:3) as the eluent. 30.4 g (51%) of 3',4'-dichloro-3-(1,3-dioxolan-2-yl)propiophenone were isolated as a yellow-orange oil.

b) 3',4'-Dichloro-3-(1,3-dioxolan-2-yl)propiophenone (10.0 g) was dissolved in 20 ml of acetic acid and added under argon and while stirring to a solution of 7.4 g of N-acetylethylenediamine in 80 ml of acetic acid. The reaction mixture was heated to reflux overnight, the acetic acid was subsequently removed in a vacuum. The residue was taken up in 200 ml of methylene chloride and washed with a mixture of 100 ml of saturated sodium hydrogen carbonate solution and 100 ml of 2N sodium hydroxide solution. The aqueous phase was back-extracted twice with 100 ml of methylene chloride each time, the organic phases were combined, dried with $MgSO_4$ and freed from solvent. The residue, 12.5 g of dark brown oil were chromatographed on 500 g of silica gel with ethyl acetate as the eluent. 9.1 g (84%) of N-[2-[2-(3,4-dichlorophenyl)-pyrrol-1-yl]ethyl]acetamide were isolated as a yellow-brown oil. MS: m/e=296, 298, 300 (9:6:1, M+).

c) N-[2-[2-(3,4-Dichlorophenyl)-pyrrol-1-yl]ethyl]-acetamide (4.6 g) was treated with 25 ml of phosphorus oxychloride under argon and boiled for 1 hour while stirring. The reaction mixture was hydrolyzed at 0° C. with 70 ml of 2N sodium hydroxide solution and 120 ml of 28% sodium hydroxide solution, diluted with 1400 ml of water and extracted with methylene chloride (1×500 ml, 2×250 ml). The organic extracts were combined, dried with $MgSO_4$ and freed from solvent. 2.0 g of a total of 3.8 g of crude product were dissolved in a 20-fold amount of ethanol and treated with 1.1 equivalents of a saturated solution of fumaric acid in ethanol. There were obtained 2.1 g (65%) of 6-(3,4-dichlorophenyl)-3,4-dihydro-1-methylpyrrolo[1,2-a]pyrazine fumarate (1:1); m.pt.: 193°–195° C. (dec.).

EXAMPLE 6 a) 2-(2-Bromoethyl)-1,3-dioxolane (44.3 ml) was added dropwise within 15 minutes under argon and while stirring at a maximum 30° C. to a suspension of Rieke magnesium, prepared from 50.8 g of magnesium chloride, in 1600 ml of absolute tetrahydrofuran. The suspension was stirred at room temperature for 15 minutes, cooled to 0° C. and, after the addition of 49.3 g of copper(I) bromide, stirred at 0° C. for 15 minutes. After cooling to −70° C. 38.5 ml of p-toluoyl chloride were added dropwise within 20 minutes. The reaction mixture was stirred at −70° C. for 30 minutes and at room temperature for 2 hours and subsequently hydrolyzed with 1000 ml of saturated ammonium chloride solution while cooling at a maximum 20° C. After the addition of 500 ml of water the mixture was extracted once with 1000 ml of ethyl acetate and twice with 500 ml of ethyl acetate each time. The combined organic extracts were dried over $MgSO_4$ and freed from solvent. 71.0 g of brown oil were chromatographed on 1500 g of silica gel with ethyl acetate/hexane/methylene chloride (1:4:1) as the eluent. 21.8 g (34%) of 3-(1,3-dioxolan-2-yl)-4'-methylpropiophenone were isolated as a yellow-orange oil.

b) 3-(1,3-Dioxolan-2yl)-4'-methylpropiophenone (10.2 g) was dissolved in 20 ml of acetic acid and added under argon and while stirring to a solution of 9.4 g of N-acetylethylenediamine in 100 ml of acetic acid. The reaction mixture was heated to reflux overnight, the acetic acid was subsequently removed in a vacuum. The residue was taken up in 200 ml of methylene chloride and washed with a mixture of 100 ml of saturated sodium hydrogen carbonate solution and 150 ml of 2N sodium hydroxide solution. The aqueous phase was back-extracted twice with 100 ml of methylene chloride each time. The organic phases were combined, dried with $MgSO_4$ and freed from solvent. The residue, 14.0 g of dark brown oil were chromatographed on 550 g of silica gel with ethyl acetate/hexane (2:1) as the eluent. 7.8 g (70%) of N-[2-(2-p-tolylpyrrol-1-yl)ethyl]acetamide were isolated as a brown oil. MS: m/e=242 (M+).

c) N-[2-(2-p-Tolylpyrrol-1-yl)ethyl]acetamide (3.9 g) was treated with 20 ml of phosphorus oxychloride under argon and boiled for ½ hour while stirring. The reaction mixture was hydrolyzed at 0° C. with 100 ml of 2N sodium hydroxide solution and 100 ml of 28% sodium hydroxide solution, diluted with 1000 ml of water and extracted with methylene chloride (1×200 ml, 2×100 ml). The organic extracts were combined, dried with $MgSO_4$ and freed from solvent. 1.7 g of a total of 3.5 g of crude product were dissolved in a 25-fold amount of ethanol and treated with 1.1 equivalents of a saturated solution of fumaric acid in ethanol. There were obtained 1.8 g (68%) of 3,4-dihydro-1-methyl-6-p-tolylpyrrolo[1,2-a]pyrazine fumarate (1:1); m.pt.: 186°–189° C. (dec.).

EXAMPLE 7 a) 1,1'-Carbonyl-diimidazole (48.8 g) was added portionwise within 30 minutes under argon and while stirring to a suspension of 50.0 g of 3,4-methylenedioxybenzoic acid in 500 ml of methylene chloride. The resulting clear solution was stirred at room temperature for 2 hours and added dropwise within 30 minutes to 42 ml of triethylamine. Thereafter, 29.4 g of N,O-dimethylhydroxylamine hydrochloride were added and the mixture was stirred at room temperature overnight. After the addition of 800 ml of 30% citric acid solution the mixture was extracted twice with 300 ml of methylene chloride each time. The organic phases were washed in succession with 300 ml of 30% citric acid solution, 500 ml of saturated sodium hydrogen carbonate solution and 300 ml of saturated sodium hydrogen carbonate solution. The organic phases were combined, dried with $MgSO_4$ and freed from solvent. 60.9 g (97%) of N-methoxy-N-methyl-1,3-benzodioxol-5-carboxamide were isolated as a pale yellow oil.

b) 2-(2-Bromoethyl)-1,3-dioxolane (4.5 ml) was added dropwise within 15 minutes under argon and while stirring at a maximum 30° C. to a suspension of Rieke magnesium, prepared from 5.1 g of magnesium chloride, in 150 ml of absolute tetrahydrofuran. The suspension was stirred at room temperature for 30 minutes, cooled to −70° C. and treated within 10 minutes with 6.1 g of N-methoxy-N-methyl-1,3-benzodioxol-5-carboxamide. The reaction mixture was stirred at −70° C. for 30 minutes and at room temperature for 2 hours and subsequently hydrolyzed with 100 ml of saturated ammonium chloride solution while cooling at a maximum 20° C. After the addition of 50 ml of water the mixture was extracted once with 150 ml of ethyl acetate and twice with 100 ml of ethyl acetate each time. The combined organic extracts were dried over MgSO$_4$ and freed from solvent. The residue, 8.0 g of yellow oil, was chromatographed on 490 g of silica gel with ethyl acetate/hexane (1:5) as the eluent. 5.3 g (72%) of 1-(1,3-benzodioxol-5-yl)-3-(1,3-dioxol-2-yl)-1-propanone were isolated as a colourless solid. A sample crystallized colourless from a 20-fold amount of diethyl ether and melted at 94°-96° C.

c) 1-(1,3-Benzodioxol-5-yl)-3-(1,3-dioxol-2-yl)-1-propanone (1.7 g) was added under argon and while stirring to a solution of 1.4 g of N-acetylethylenediamine in 20 ml of acetic acid. The reaction mixture was refluxed overnight, the acetic acid was subsequently removed in a vacuum. The residue was taken up in 80 ml of methylene chloride and washed with a mixture of 50 ml of saturated sodium hydrogen carbonate solution and 10 ml of 2N sodium hydroxide solution. The aqueous phase was back-extracted twice with 50 ml of methylene chloride each time, the organic phases were combined, dried with MgSO$_4$ and freed from solvent. The residue, 2.6 g of brown oil, was chromatographed on 50 g of silica gel with ethyl acetate/hexane (2:1) as the eluent. 1.7 g (95%) of N-[2-[2-(1,3-benzodioxol-5-yl)-pyrrol-1-yl]-ethyl]acetamide were isolated as a yellow oil. MS: m/e=272 (M+).

d) N-[2-[2-(1,3-Benzodioxol-5-yl)-pyrrol-1-yl]-ethyl]acetamide (1.7 g) was treated with 10 ml of phosphorus oxychloride under argon and boiled for 45 minutes while stirring. The reaction mixture was hydrolyzed at 0° C. with 50 ml of 2N sodium hydroxide solution and 50 ml of 28% sodium hydroxide solution, diluted with 600 ml of water and extracted with methylene chloride (1×100 ml, 2×60 ml). The organic extracts were combined, dried with MgSO$_4$ and freed from solvent. 1.4 g of crude product was dissolved in a 20-fold amount of ethanol and treated with 1.1 equivalents of a saturated solution of fumaric acid in ethanol. There were obtained 1.5 g (66%) of 6-(1,3-benzodioxol-5-yl)-3,4-dihydro-1-methylpyrrolo[1,2-a]pyrazine fumarate (1:1); m.pt.: 191°-193° C. (dec.).

EXAMPLE 8 a) 2-(2-Bromoethyl)-1,3-dioxolane (38 ml) was added dropwise within 15 minutes under argon and while stirring at a maximum 30° C. to a suspension of Rieke magnesium, prepared from 43.5 g of magnesium chloride, in 1300 ml of absolute tetrahydrofuran. The suspension was stirred at room temperature for 30 minutes, cooled to 0° C. and, after the addition of 42.2 g of copper(I) bromide, stirred at 0° C. for 15 minutes. After cooling to −70° C. 50.0 g of 3,4-dimethoxybenzoyl chloride in 200 ml of absolute tetrahydrofuran were added dropwise within 20 minutes. The reaction mixture was stirred at −70° C. for 30 minutes and at room temperature for 2 hours and subsequently hydrolyzed with 1000 ml of saturated ammonium chloride solution while cooling at a maximum 20° C. After the addition of 500 ml of water the mixture was extracted three times with ethyl acetate (1×1000 ml, 2×500 ml). The combined organic extracts were washed with 1000 ml of saturated sodium chloride solution, dried over MgSO$_4$ and freed from solvent. The residue, 69.5 g of dark brown oil, was chromatographed on 1000 g of silica gel with ethyl acetate/hexane (1:1) as the eluent. There were obtained 26.5 g of crude product which were dissolved in a 12-fold amount of n-hexane with the addition of 100 ml of methylene chloride. 50 ml of methylene chloride were distilled off. 22.3 g (34%) of 3-(1,3-dioxolan-2-yl)-3',4'-dimethoxypropiophenone were isolated as colourless crystals which melted at 103°-105° C.

b) 3-(1,3-Dioxolan-2-yl)-3',4'-dimethoxypropiophenone (6.3 g) was dissolved in 30 ml of acetic acid and added under argon and while stirring to a solution of 4.9 g of N-acetylethylenediamine in 50 ml of acetic acid. The reaction mixture was heated to reflux overnight, the acetic acid was subsequently removed in a vacuum. The residue was taken up in 150 ml of methylene chloride and washed with a mixture of 100 ml of saturated sodium hydrogen carbonate solution and 150 ml of 2N sodium hydroxide solution. The aqueous phase was back-extracted three times with 100 ml of methylene chloride each time, the organic phases were combined, dried with MgSO$_4$ and freed from solvent. The residue, 7.3 g of dark brown oil, was chromatographed on 250 g of silica gel with ethyl acetate as the eluent. 2.6 g (38%) of N-[2-[2-(3,4-dimethoxyphenyl)pyrrol-1-yl]-ethyl]acetamide were isolated as a brown oil.

c) N-[2-[2-(3,4-Dimethoxyphenyl)pyrrol-1-yl]-ethyl]-acetamide (2.6 g) was treated with 20 ml of phosphorus oxychloride under argon and boiled for 1 hour while stirring. The reaction mixture was hydrolyzed at 0° C. with 100 ml of 2N sodium hydroxide solution and 100 ml of 28% sodium hydroxide solution, diluted with 1200 ml of water and extracted with methylene chloride (1×200 ml, 2×100 ml). The organic extracts were combined, dried with MgSO$_4$ and freed from solvent. 1.4 g of a total of 2.7 g of crude product were chromatographed on 30 g of silica gel with methylene chloride/methanol (19:1) as the eluent. The product, 0.8 g of brown oil, was dissolved in a 40-fold amount of ethanol, treated with 1.1 equivalents of a saturated solution of fumaric acid in ethanol and concentrated to a volume of 10 ml. There was obtained 0.8 g of 6-(3,4-dimethoxyphenyl)-3,4-dihydro-1-methylpyrrolo[1,2-a]pyrazine fumarate (1:1.3); m.pt.: 158°-160° C. (dec.). A sample was recrystallized from a 40-fold amount of ethanol and yielded the (1:1) fumarate which melted at 160°-161° C. with decomposition.

EXAMPLE 9 a) 4,4-Dimethoxy-1-phenyl-1-butanone (E/Z)-dimethylhydrazone (5.0 g) dissolved in 20 ml of tetrahydrofuran was treated with 40 ml of 2N hydrochloric acid solution under argon in such a manner that the temperature did not rise above 10° C. (ice bath). The reaction mixture was stirred at room temperature for 3 hours and then extracted three times with 25 ml of ethyl acetate each time. The organic phases were combined, dried over MgSO$_4$ and freed from solvent. The brown, oily residue (2.5 g) was dissolved in 5 ml of acetic acid without further purification and added under argon and while stirring at room temperature to a solution of 3.2 g of N-acetylethylenediamine in 15 ml of acetic acid. The mixture was stirred at room temperature for ½ hour and the acetic acid was subsequently removed in a vacuum at 37° C. The residue was taken up in methylene chloride, washed with saturated sodium hydrogen carbonate solution and water, dried with MgSO$_4$ and freed from solvent. The crude product, 3.0 g of brown oil, was chromatographed on 250 g of silica gel with ethyl acetate/hexane (1:1) as the eluent. 1.3 g (37%) of N-[2-(2-phenylpyrrol-1-yl)ethyl]acetamide were isolated as a yellow, amorphous solid. MS: m/e=228 (M+).

b) N-[2-(2-Phenylpyrrol-1-yl]-ethyl]acetamide (5.0 g) was added to 30 ml of phosphorus oxychloride under argon and the mixture was boiled under reflux for 1 hour. The cooled mixture was hydrolyzed with 100 ml of 2N sodium hydroxide solution and 230 ml of 28% sodium hydroxide solution (cooling with ice), diluted with 2000 ml of water and extracted with methylene chloride (1×350 ml, 3×200 ml). The organic phases were combined, dried with MgSO$_4$ and freed from solvent. 1.0 g of a total of 4.5 g of crude product was dissolved in a 30-fold amount of ethanol and treated with 1.1 equivalents of a saturated solution of fumaric acid in ethanol. There was obtained 0.9 g (57%) of 3,4-dihydro-1-methyl-6-phenylpyrrolo[1,2-a]pyrazine fumarate (1:1); m.pt.: 175° C. (dec.).

EXAMPLE 10 a) Molecular sieve 4 Å and 14.9 g of N-acetylethylenediamine (200 g) was added in succession under argon to a solution of 27.5 g of 1,2,3,4-tetrahydro-1-oxo-2-naphthaleneacetaldehyde in 275 ml of diethyl ether. The reaction mixture was stirred at boiling temperature for 5 hours and subsequently cooled. The molecular sieve was filtered off, the filtrate was freed from solvent and the crude product was chromatographed on 600 g of silica gel with ethyl acetate as the eluent. There were obtained 23.5 g (79%) of N-[2-(4,5-dihydro-1H-benzo[g]indol-1-yl)ethyl]-acetamide with a melting point of 95°-96° C. (ethyl acetate).

b) N-[2-(4,5-Dihydro-1H-benzo[g]indol-1-yl)ethyl]-acetamide (5.3 g) was stirred with 60 ml of phosphorus oxychloride at room temperature for 1 hour. The reaction mixture was hydrolyzed at 0° C. with 500 ml of 28% sodium hydroxide solution, diluted with 4000 ml of water and extracted three times with 300 ml of methylene chloride each time. The organic phases were combined, dried with MgSO$_4$ and freed from solvent. 2.0 g of a total of 5.0 g of crude product were dissolved in a 30-fold amount of ethanol and treated with 1.1 equivalents of a saturated solution of fumaric acid in ethanol. There were obtained 2.3 g (67%) of 5,6,10,11-tetrahydro-8-methyl-benzo[g]pyrazino[1,2-a]indole fumarate (2:3); m.pt.: 181° C. (dec.).

EXAMPLE 11 a) 5-Chloro-3,4-dihydro-1(2H)-naphthalenone (44.1 g) was suspended in 200 ml of ethanol under argon, treated with 55.7 ml of N,N-dimethylhydrazine (asym.) and boiled under reflux for 96 hours. The reaction mixture was freed from solvent and excess dimethylhydrazine in a vacuum. The residue was taken up in 300 ml of methylene chloride, dried with MgSO$_4$ and freed from solvent. 52.8 g (97%) of 5-chloro-3,4-dihydro-1(2H)-naphthalenone N',N'-dimethylhydrazone were processed without further purification.

b) 5-Chloro-3,4-dihydro-1(2H)-naphthalenone N',N'-dimethylhydrazone (52.8 g) was dissolved in 800 ml of absolute tetrahydrofuran under argon and treated with 43 ml of N,N,N',N'-tetramethylethylenediamine. The reaction solution was cooled to −70° C. and 150 ml of a 1.6N solution of n-butyllithium in hexane were added dropwise while stirring within 45 minutes. The mixture was stirred at −70° C. for a further 30 minutes and then 34 ml of bromo-acetaldehyde dimethyl acetal were added dropwise at −30° C. within 15 minutes. Subsequently, the mixture was stirred at −30° C. for 2 hours and at room temperature for 16 hours. The reaction mixture was hydrolyzed with 1000 ml of water, extracted once with 1000 ml of ethyl acetate and twice with 500 ml of ethyl acetate each time. The combined organic extracts were dried over MgSO$_4$ and freed from solvent. The crude product, 81.1 g of brown oil, was chromatographed on 2000 g of silica gel with hexane/ethyl acetate mixtures (6:1 to 1:2) as the eluent. There were obtained 47.5 g (64%) of 5-chloro-1-(dimethylhydrazono)-1,2,3,4-tetrahydro-2-naphthaleneacetaldehyde dimethyl acetal.

c) 5-Chloro-1-(dimethylhydrazono)-1,2,3,4-tetrahydro-2-naphthaleneacetaldehyde dimethyl acetal (47.5 g) was dissolved under argon in a mixture of 2300 ml of tetrahydrofuran and 780 ml of 0.067M phosphate buffer of pH value 7. The solution was treated with 26.1 g of copper(II) chloride dihydrate and stirred at room temperature for 16 hours. 2000 ml of ethyl acetate were added to the reaction mixture and it was washed three times with 2000 ml of a mixture of 25% ammonia solution and saturated ammonium chloride solution (1:19) each time. The aqueous wash phases were extracted once with 1500 ml of ethyl acetate and once with 1000 ml of ethyl acetate, the organic phases were combined, dried over MgSO$_4$ and freed from solvent. There were obtained 42.2 g of crude 5-chloro-1,2,3,4-tetrahydro-1-oxo-2-naphthaleneacetaldehyde dimethyl acetal which was processed without purification.

d) For the cleavage of the acetal, 160 ml of a 10% aqueous oxalic acid solution were applied to 1000 g of silica gel and 42.2 g of 5-chloro-1,2,3,4-tetrahydro-1-oxo-2-naphthalene-acetaldehyde dimethyl acetal were chromatographed on this mixture with methylene chloride as the eluent. There were obtained 30.8 g (88% based on the product of Example 11.b) of 5-chloro-1,2,3,4-tetrahydro-1-oxo-2-naphthaleneacetaldehyde.

e) N-Acetylethylenediamine (15.5 g) was dissolved in 300 ml of methylene chloride under argon, treated in succession with 260 g of molecular sieve 4 Å and a solution of 30.8 g of 5-chloro-1,2,3,4-tetrahydro-1-oxo-2-naphthaleneacetaldehyde in 150 ml of methylene chloride and refluxed for 23 hours while stirring. The reaction mixture was cooled, filtered over a Celite ® pad and the filtrate was freed from solvent. The crude product, 37.5 g of brown, amorphous material, was dissolved in a 6-fold amount of hot ethyl acetate and, after the addition of an 8-fold amount of hexane boiled briefly. There were obtained 29.4 g (74%) of N-[2-(6-chloro-4,5-dihydro-1H-benz[g]indol-1-yl)-ethyl]acetamide; m.pt.: 124°-126° C.

f) N-[2-(6-Chloro-4,5-dihydro-1H-benz[g]indol-1-yl)ethyl]acetamide (6.0 g) was treated with 30 ml of phosphorus oxychloride and the mixture was stirred at 100° C. for 30 minutes. The cooled mixture was added to 2500 g of ice-water and treated with 100 ml of 2N sodium hydroxide solution and 200 ml of 28% sodium hydroxide solution. The mixture was extracted once with 300 ml of methylene chloride and twice with 100 ml of methylene chloride each time, the organic phases were combined, dried with MgSO$_4$ and freed from solvent. 5.7 g of residue were dissolved in a 20-fold amount of hot ethanol and treated while hot with 1.1 equivalents of a saturated solution of fumaric acid in ethanol. There were obtained 6.6 g (82%) of 4-chloro-5,6,10,11-tetrahydro-8-methylbenz[g]pyrazino[1,2-a]indole fumarate (1:1); m.pt.: 191°-192° C. (dec.).

EXAMPLE 12 a) 6-Chloro-3,4-dihydro-1(2H)-naphthalenone (11.0 g) was suspended in 150 ml of ethanol under argon, treated with 18.5 ml of N,N-dimethylhydrazine (asym.) and boiled under reflux for 72 hours. The reaction mixture was freed from solvent and excess dimethylhydrazine in a vacuum. The residue was taken up in 200 ml of methylene chloride, dried with MgSO$_4$ and freed from solvent. The residue was distilled and yielded 12.6 g (93%) of 6-chloro-3,4-dihydro-1(2H)-naphthalenone N',N'-dimethylhydrazone of b.pt.: 85°-87° C./0.06 mbar.

b) 6-Chloro-3,4-dihydro-1(2H)-naphthalenone N',N'-dimethylhydrazone (12.6 g) was dissolved in 200 ml of absolute tetrahydrofuran under argon and treated with 10.2 ml of N,N,N',N'-tetramethylethylenediamine. The reaction solution was cooled to −70° C. and 36 ml of a 1.6N solution of n-butyllithium in hexane were added dropwise within 15 minutes while stirring. The mixture was stirred at −70° C. for a further 15 minutes and then 8.0 ml of bromoacetaldehyde dimethyl acetal were added dropwise at −30° C. within 15 minutes. Subsequently, the mixture was stirred at −30° C. for 2 hours and at room temperature for 18 hours. The reaction mixture was hydrolyzed with 400 ml of water, extracted once with 300 ml of ethyl acetate and twice with 150 ml of ethyl acetate each time. The combined organic extracts were dried over MgSO$_4$ and freed from solvent. The crude product, 18.8 g of brown oil, was chromatographed on 400 g of silica gel with ethyl acetate/hexane (1:6) as the eluent. There were obtained 10.8 g (61%) of 6-chloro-1-(dimethylhydrazono)-1,2,3,4-tetrahydro-2-naphthaleneacetaldehyde dimethyl acetal.

c) 6-Chloro-1-(dimethylhydrazono)-1,2,3,4-tetrahydro-2-naphthaleneacetaldehyde dimethyl acetal (10.3 g) was dissolved under argon in a mixture of 500 ml of tetrahydrofuran and 265 ml of 0.067M phosphate buffer of pH value 7. The solution was treated with 8.7 g of copper(II) chloride dihydrate and stirred at room temperature for 18 hours. 400 ml of ethyl acetate were added to the reaction mixture and it was washed twice with 500 ml of a mixture of 25% ammonia solution and saturated ammonium chloride solution (1:19) each time. The aqueous wash phases were extracted three times with 200 ml of ethyl acetate each time, the organic phases were combined, dried over MgSO$_4$ and freed from solvent. The crude product, 8.2 g of brown oil, was chromatographed on 330 g of silica gel with ethyl acetate/hexane mixtures (1:6 to 1:4) as the eluent. There were obtained 2.1 g (24%) of 6-chloro-1,2,3,4-tetrahydro-1-oxo-2-naphthaleneacetaldehyde dimethyl acetal besides 3.2 g (43%) of 6-chloro-1,2,3,4-tetrahydro-1-oxo-2-naphthaleneacetaldehyde.

d) For the cleavage of the acetal, 8 ml of 10% aqueous oxalic acid solution were applied to 50 g of silica gel and 2.1 of 6-chloro-1,2,3,4-tetrahydro-1-oxo-2-naphthaleneacetaldehyde dimethyl acetal were chromatographed on this mixture with methylene chloride as the eluent. There were obtained 1.7 g (98%) of 6-chloro-1,2,3,4-tetrahydro-1-oxo-2-naphthalene-acetaldehyde.

e) N-Acetylethylenediamine (2.4 g) was dissolved in 40 ml of methylene chloride under argon, treated in succession with 40 g of molecular sieve 4 Å and a solution of 4.8 g of 6-chloro-1,2,3,4-tetrahydro-1-oxo-2-naphthaleneacetaldehyde in 20 ml of methylene chloride and refluxed for 40 hours while stirring. The reaction mixture was cooled, filtered over a Celite ® pad and the filtrate was freed from solvent. The crude product, 5.6 g of brown solid, was dissolved in a 6-fold amount of hot ethyl acetate and, after the addition of an 8-fold amount of hexane, boiled briefly. There were obtained 4.2 g (67%) of N-[2-(7-chloro-4,5-dihydro-1H-benz[g]indol-1-yl)ethyl]acetamide; m.pt.: 144°-145° C.

f) N-[2-(7-Chloro-4,5-dihydro-1H-benzo[g]indol-1-yl)ethyl]acetamide (2.8 g) was treated with 20 ml of phosphorus oxychloride under argon and the mixture was stirred at 100° C. for 30 minutes. The cooled mixture was added to 1500 g of ice-water and treated with 100 ml of 2N sodium hydroxide solution and 150 ml of 28% sodium hydroxide solution. The mixture was extracted once with 300 ml of methylene chloride and twice with 100 ml of methylene chloride each time, the organic phases were combined, dried with MgSO$_4$ and freed from solvent. The residue (2.6 g) was dissolved in a 20-fold amount of hot ethanol and treated while hot with 1.1 equivalents of a saturated solution of fumaric acid in ethanol. There were obtained 3.3 g (88%) of 3-chloro-5,6,10,11-tetrahydro-8-methylbenzo[g]pyrazino[1,2-a]indole fumarate (1:1); m.pt. 195°-196° C. (dec.).

EXAMPLE 13 a) 7-Chloro-3,4-dihydro-1(2H)-naphthalenone (20.0 g) was suspended in 80 ml of ethanol under argon, treated with 34 ml of N,N-dimethylhydrazine (asym.) and boiled under reflux for 72 hours. The reaction mixture was freed from solvent and excess dimethylhydrazine in a vacuum. The residue was taken up in 130 ml of methylene chloride, dried with MgSO$_4$ and freed from solvent. The residue was distilled and yielded 20.3 g (82%) of 7-chloro-3,4-dihydro-1(2H)-naphthalenone N',N'-dimethyl-hydrazone of b.pt.: 78°-85° C./0.035 mbar.

b) 7-Chloro-3,4-dihydro-1(2H)-naphthalenone N',N'-dimethylhydrazone (20.3 g) was dissolved in 400 ml of absolute tetrahydrofuran under argon and treated with 16.4 ml of N,N,N',N'-tetramethylethylenediamine. The reaction solution was cooled to −70° C. and 60 ml of a 1.6N solution of n-butyllithium in hexane were added dropwise while stirring within 15 minutes. The mixture was stirred at −70° C. for a further 15 minutes and then 12.9 ml of bromoacetaldehyde dimethyl acetal were added dropwise at −30° C. within 15 minutes. Subsequently, the mixture was stirred at −30° C. for 2 hours and at room temperature for 20 hours. The reaction mixture was hydrolyzed with 500 ml of water, extracted once with 400 ml of ethyl acetate and twice with 250 ml of ethyl acetate each time. The combined organic extracts were dried over MgSO$_4$ and freed from solvent. The crude product, 29.9 g of dark brown oil, was chromatographed on 550 g of silica gel with ethyl acetate/hexane mixtures (1:6 to 1:5) as the eluent. There were obtained 16.0 g (57%) of 7-chloro-1-(dimethylhydrazono)-1,2,3,4-tetrahydro-2-naphthaleneacetaldehyde dimethyl acetal.

c) 7-Chloro-1-(dimethylhydrazono)-1,2,3,4-tetrahydro-2-naphthaleneacetaldehyde dimethyl acetal (16.0 g) was dissolved under argon in 700 ml of tetrahydrofuran and 180 ml of water. The solution was treated in succession with 30.8 g of sodium (meta)periodate, 11.8 g of sodium acetate and 120 ml of acetic acid and stirred at 50° C. for 18 hours. Subsequently, 2000 ml of water were added and the mixture was extracted three times with 500 ml of ethyl acetate each time. The organic phases were washed with 500 ml of a saturated sodium chloride solution, combined, dried over $MgSO_4$ and freed from solvent. The crude product, 18.4 g of dark brown oil, was chromatographed on 500 g of silica gel with ethyl acetate/hexane (1:3) as the eluent. There were obtained 4.8 g (35%) of 7-chloro-1,2,3,4-tetrahydro-1-oxo-2-naphthaleneacetaldehyde dimethyl acetal.

d) For the acetal cleavage, 15 ml of a 10% aqueous oxalic acid solution were applied to 100 g of silica gel and 4.8 g of 7-chloro-1,2,3,4-tetrahydro-1-oxo-2-naphthaleneacetaldehyde dimethyl acetal were chromatographed on this mixture with methylene chloride as the eluent. There were obtained 3.8 g (95%) of 7-chloro-1,2,3,4-tetrahydro-1-oxo-2-naphthalene-acetaldehyde.

e) N-Acetylethylenediamine (2.9 g) was dissolved in 50 ml of methylene chloride under argon, treated in succession with 4.5 g of molecular sieve 4 Å and a solution of 5.7 g of 7-chloro-1,2,3,4-tetrahydro-1-oxo-2-naphthaleneacetaldehyde in 20 ml of methylene chloride and heated to reflux for 16 hours while stirring. The reaction mixture was cooled, filtered over a Celite ® pad and the filtrate was freed from solvent. The crude product, 6.6 g of brown solid, was dissolved in a 6-fold amount of hot ethyl acetate and, after the addition of an 8-fold amount of hexane, boiled briefly. There were obtained 4.0 g (55%) of N-[2-(8-chloro-4,5-dihydro-1H-benzo[g]indol-1-yl)ethyl]acetamide; m.pt.: 144°–146° C.

f) N-[2-(8-Chloro-4,5-dihydro-1H-benzo[g]indol-1-yl)-ethyl]acetamide (2.9 g) was treated with 20 ml of phosphorus oxychloride under argon and the mixture was stirred at 100° C. for 30 minutes. The cooled mixture was poured on to 1500 g of ice-water and treated with 100 ml of 2N sodium hydroxide solution and 150 ml of 28% sodium hydroxide solution. The mixture was extracted once with 250 ml of methylene chloride and twice with 150 ml of methylene chloride each time, the organic phases were combined, dried with $MgSO_4$ and freed from solvent. The residue (2.7 g) was dissolved in a 20-fold amount of ethanol and treated while hot with 1.1 equivalents of a saturated solution of fumaric acid in ethanol. There were obtained 3.2 g (83%) of 2-chloro-5,6,10,11-tetrahydro-8-methylbenzo[g]pyrazino[1,2-a]indole fumarate (1:1); m.pt.: 172°–174° C. (dec.).

EXAMPLE 14 a) 3,4-Dihydro-4-methyl-1(2H)-naphthalenone N',N'-dimethylhydrazone (31.4 g) was dissolved in 500 ml of absolute tetrahydrofuran under argon and treated with 28 ml of N,N,N',N'-tetramethylethylenediamine. The reaction solution was cooled to −70° C. and 98 ml of a 1.6N solution of n-butyllithium in hexane were added dropwise while stirring within 30 minutes. The mixture was stirred at −70° C. for a further 30 minutes and then 22 ml of bromo- acetaldehyde dimethyl acetal were added dropwise at −30° C. within 10 minutes. Subsequently, the mixture was stirred at −30° C. for 2 hours and at room temperature for 18 hours. The reaction mixture was hydrolyzed with 500 ml of water and extracted three times with 300 ml of ethyl acetate each time. The combined organic extracts were dried over $MgSO_4$ and freed from solvent. The crude product, 50.3 g of brown oil, was chromatographed on 1000 g of silica gel with hexane/diethyl ether mixtures (14:1 to 1:2) as the eluent. There were obtained 23.1 g (51%) of 1-(dimethylhydrazono)-1,2,3,4-tetrahydro-4-methyl-2-naphthaleneacetaldehyde dimethyl acetal.

b) 1-(Dimethylhydrazono)-1,2,3,4-tetrahydro-4-methyl-2-naphthaleneacetaldehyde dimethyl acetal (23.1 g) was dissolved under argon in a mixture of 1000 ml of tetrahydrofuran and 350 ml of 0.067M phosphate buffer of pH value 7. The solution was treated with 13.6 g of copper(II) chloride dihydrate and stirred at room temperature for 16 hours. 500 ml of ethyl acetate were added to the reaction mixture and it was washed three times with a mixture of 25% ammonia solution and saturated ammonium chloride solution (1:19) (1×800 ml, 2×500 ml). The aqueous wash phases were extracted twice with 500 ml of ethyl acetate each time, the organic phases were combined, dried over $MgSO_4$ and freed from solvent. There were obtained 20.0 g of crude 1,2,3,4-tetrahydro-4-methyl-1-oxo-2-naphthaleneacetaldehyde dimethyl acetal which was processed without purification.

c) For the acetal cleavage, 100 ml of a 10% aqueous oxalic acid solution were applied to 600 g of silica gel and 20.0 g of 1,2,3,4-tetrahydro-4-methyl-1-oxo-2-naphthaleneacetaldehyde dimethyl acetal were chromatographed on this mixture with methylene chloride as the eluent. There were obtained 14.5 g (90% based on the product from Example 14.a) of 1,2,3,4-tetrahydro-4-methyl-1-oxo-2-naphthaleneacetaldehyde.

d) N-Acetylethylenediamine (8.1 g) was dissolved in 150 ml of methylene chloride under argon, treated in succession with 140 g of molecular sieve 4 Å and a solution of 14.5 g of 1,2,3,4-tetrahydro-4-methyl-1-oxo-2-naphthaleneacetaldehyde in 100 ml of methylene chloride and heated to reflux for 18 hours while stirring. The reaction mixture was cooled, filtered over a Celite ® pad and the filtrate was freed from solvent. The crude product, 19.4 g of dark brown oil, was chromatographed on 300 g of silica gel with ethyl acetate as the eluent. The product, 14.2 g of yellow-brown oil, was dissolved in 200 ml of ethanol, boiled with 0.7 g of Norite ® and, after fitration and removal of the solvent, yielded 13.9 g (72%) of N-[2-(4,5-dihydro-5-methyl-1H-benzo[g]indol-1-yl)ethyl]acetamide which was processed without further purification.

e) N-[2-(4,5-Dihydro-5-methyl-1H-benzo[g]indol-1-yl)ethyl]acetamide (5.0 g) was treated with 20 ml of phosphorus oxychloride under argon and the mixture was stirred at 100° C. for 30 minutes. The cooled mixture was added to 2000 ml of ice-water and treated with 200 ml of 28% sodium hydroxide solution. The mixture was extracted once with 300 ml of methylene chloride and twice with 100 ml of methylene chloride each time, the organic phases were combined, dried with $MgSO_4$ and freed from solvent. 4.6 g of residue were chromatographed on 200 g of silica gel with methylene chloride/methanol mixtures (49:1 to 9:1) as the eluent. Of the crude product, 3.9 g of brown oil, 1.9 g were dissolved in a 20-fold amount of ethanol and treated with 1.1 equivalents of a saturated solution of fumaric acid in ethanol. After concentration to 10 ml and addition of 10 ml of ethanol and 70 ml of ethyl acetate there separated ochre-yellow crystals which were recrystallized from an ethanol/ethyl acetate mixture (1:2, 30-fold amount).

There were obtained 1.7 g (43%) of 5,6,10,11-tetrahydro-5,8-dimethylbenzo[g]pyrazino[1,2-a]indole fumarate (2:3); m.pt.: 156°–157° C. (dec.).

EXAMPLE 15 a) N-[2-(4,5-Dihydro-1H-benzo[g]indol-1-yl)ethyl]acetamide (4.0 g) was dissolved in 50 ml of toluene under argon and treated with 3.8 g of 2,3-dichloro-5,6-dicyano-1,4-benzoquinone (DDQ). The reaction mixture was stirred at 80° C. for 2 hours, a further 0.4 g of DDQ was then added and the mixture was stirred at 80° C. for a further 2 hours. The separated precipitate was filtered off at room temperature and the filtrate was freed from solvent. The crude product, 1.5 g of dark brown solid, was chromatographed on 60 g of neutral aluminium oxide with ethyl acetate as the eluent. There were obtained 1.2 g (30%) of N-[2-(1H-benzo[g]indol-1-yl)ethyl]acet-amide which was processed without further purification.

b) N-[2-(1H-Benzo[g]indol-1-yl)ethyl]acetamide (1.4 g) was treated with 20 ml of phosphorus oxychloride under argon and the mixture was stirred at 100° C. for 30 minutes. The cooled mixture was poured on to 500 g of ice-water and treated with 150 ml of 2N sodium hydroxide solution and 50 ml of 28% sodium hydroxide solution. The mixture was extracted once with 200 ml of methylene chloride and twice with 100 ml of methylene chloride each time, the organic phases were combined, dried with MgSO4 and freed from solvent. 1.4 g of residue were dissolved in a 20-fold amount of ethanol and treated with a hot saturated solution of fumaric acid in ethanol. There were obtained 1.6 g (83%) of 10,11-dihydro-8-methylbenzo[g]pyrazino[1,2-a]indole fumarate (1:1); m.pt.: 189°–190° C. (dec.).

EXAMPLE 16 a) N-[2-(2-Phenylpyrrol-1-yl)ethyl]acetamide (0.9 g) and 5 ml of ethylene glycol was added in succession to a solution of 1.0 g of potassium hydroxide in 10 ml of water. The reaction mixture was stirred at the boiling point for 24 hours. The cold mixture was extracted twice with 50 ml of methylene chloride each time, the organic phases were combined and extracted twice with 50 ml of 2N hydrochloric acid each time. The aqueous phases were combined, brought to a pH value of 12 by the addition of 28% sodium hydroxide solution and again extracted twice with 50 ml of methylene chloride each time. The organic phases were combined, dried with MgSO4 and freed from solvent. 0.3 g of a total of 0.6 g of crude product were dissolved in a 20-fold amount of ethanol and treated with 2 equivalents of a saturated solution of fumaric acid in ethanol. There was obtained 0.3 g (64%) of 1-(2-aminoethyl)-2-phenylpyrrole fumarate (1:1); m.pt.: 169°–171° C.

b) Crude 1-(2-aminoethyl)-2-phenylpyrrole (0.3 g) was dissolved in 5 ml of acetic acid under argon and treated with 0.1 ml of a 36.5% aqueous formaldehyde solution. The reaction mixture was stirred at room temperature for 64 hours and subsequently concentrated in a vacuum. The residue was stirred briefly with 50 ml of methylene chloride and 20 ml of 10% ammonia solution. The phases were separated, the organic phase was dried with MgSO4 and freed from solvent. The residue, 0.4 g of yellow oil, was chromatographed on 70 g of silica gel with methylene chloride/methanol (49:1) as the eluent. The product, 0.3 g of yellow oil, was taken up in a 20-fold amount of ethanol and treated with 2 equivalents of a saturated solution of fumaric acid in ethanol. The separated crystals were recrystallized from ethanol. There was obtained 0.2 g (40%) of 1,2,3,4-tetrahydro-6-phenylpyrrolo[1,2-a]pyrazine fumarate (1:1); m.pt.: 182°–184° C. (dec.).

EXAMPLE 17 a) N-[2-(4,5-Dihydro-1H-benzo[g]indol-1-yl)ethyl]acetamide (5.0 g) was suspended in 60 ml of ethylene glycol and 25 ml of water under argon and treated with 5.0 g of powdered potassium hydroxide. The mixture was stirred at 120° C. for 18 hours, subsequently cooled and treated with 150 ml of 2N hydrochloric acid while cooling. The solution was washed with 200 ml of methylene chloride, the organic phase was extracted three times with 100 ml of 2N hydrochloric acid each time, the aqueous phases were combined and made strongly alkaline with 28% sodium hydroxide solution while cooling with ice. The aqueous solution was extracted once with 200 ml of methylene chloride and twice with 100 ml of methylene chloride each time, the organic phases were combined, dried with MgSO4 and freed from solvent. The residue, 4.0 g of brown oil, was chromatographed on 250 g of silica gel with methylene chloride/methanol mixtures (99:1 to 19:1) as the eluent. There were obtained 3.7 g (88%) of 1-(2-aminoethyl)-4,5-dihydro-1H-benzo[g]indole which was processed without further purification.

b) 36% aqueous formaldehyde solution (1.4 ml) was added under argon to a solution of 3.7 g of 1-(2-aminoethyl)-4,5-dihydro-1H-benzo[g]indole in 70 ml of ethanol. The reaction solution was stirred under reflux for 2 hours, subsequently cooled and freed from solvent. The residue was chromatographed on 250 g of silica gel with methylene chloride/methanol (49:1) as the eluent. 1.3 g of a total of 2.8 g of product were dissolved in a 20-fold amount of hot ethanol and treated while hot with 1.1 equivalents of a saturated solution of fumaric acid in ethanol. The precipitated solid was boiled in a 150-fold amount of methanol, filtered while hot and concentrated to a 60-fold amount of solvent. There were obtained 1.2 g (53%) of 5,6,8,9,10,11-hexahydrobenzo[g]pyrazino[1,2-a]indole fumarate (2:1); m.pt.: 183°–184° C. (dec.).

EXAMPLE 18 a) 3-Phenylfuran (4.3 g) was dissolved in 80 ml of acetonitrile under argon and treated while stirring with 8.6 g of the mixed anhydride from acetic acid and p-toluenesulphonic acid. The reaction solution was stirred at room temperature for 64 hours and subsequently stirred with 150 ml of saturated sodium hydrogen carbonate solution and 150 ml of diethyl ether 30 minutes. The phases were separated and the aqueous phase was extracted once with a further 100 ml of diethyl ether. The organic phases were combined, washed with 100 ml of water, dried over MgSO4 and freed from solvent. The residue was chromatographed on 200 g of silica gel with methylene chloride/hexane (1:1) as the eluent. There was obtained 0.7 g (13%) of 2-acetyl-4-phenylfuran besides 2.4 g (43%) of 3-acetyl-3-phenylfuran. The former was processed without further purification.

b) 2-Acetyl-4-phenylfuran (0.7 g) was heated at 100° C. for 1 hour under argon with 0.8 ml of 1,2-ethanediamine and 0.1 ml of water. After cooling 50 ml of water were added and the mixture was extracted three times with 50 ml of methylene chloride each time. The organic phases were combined, dried with MgSO4 and freed from solvent. The residue, 0.7 g of brown oil, was chromatographed on 60 g of silica gel with methylene chloride/methanol (19:1) as the eluent. The crude product, 0.4 g of brown solid, was dissolved in a 50-fold amount of hot ethanol and treated with 1.1 equivalents of a saturated solution of fumaric acid in ethanol. There was obtained 0.4 g (31%) of 3,4-dihydro-1-methyl-7-phenylpyrrolo[1,2-a]pyrazine fumarate (1:1); m.pt.: 181° C. (dec.)

EXAMPLE 19

3,4-Dihydro-1-methyl-6-phenylpyrrolo[1,2-a]pyrazine (1.1 g) was dissolved in a mixture of 50 ml of methanol and 5 ml of water under argon. The solution was treated portionwise with 0.9 g of sodium borohydride while stirring and stirred at room temperature overnight. Thereafter, the methanol was removed in a vacuum, the residue was taken up in 100 ml of methylene chloride and washed with 100 ml of 10% ammonia solution. The phases were separated and the aqueous phase was extracted twice with 50 ml of methylene chloride each time. The organic phases were combined, dried with MgSO₄ and freed from solvent. The crude product, 1.1 g of yellow oil, was dissolved in a 10-fold amount of ethanol and boiled briefly with 1.1 equivalents of a saturated solution of fumaric acid in ethanol. The separated colourless crystals were recrystallized from a 30-fold amount of methanol. There was obtained 0.5 g (37%) of 1,2,3,4-tetrahydro-1-methyl-6-phenylpyrrolo[1,2-a]pyrazine fumarate (1:1); m.pt.: 153°–154° C. (dec.).

EXAMPLE 20

6-(m-Chlorophenyl)-3,4-dihydro-1-methylpyrrolo[1,2-a]pyrazine (2.0 g) was dissolved in a mixture of 100 ml of methanol and 10 ml of water under argon. The solution was treated portionwise with 0.9 g of sodium borohydride while stirring and stirred at room temperature overnight. Thereafter, the methanol was removed in a vacuum, the residue was taken up in 150 ml of methylene chloride and washed with 50 ml of 10% ammonia solution. The phases were separated and the aqueous phase was extracted twice with 70 ml of methylene chloride each time. The organic phases were combined, dried with MgSO₄ and freed from solvent. The crude product, 2.0 g of yellow oil, was dissolved in a 20-fold amount of ethanol and treated with 1.1 equivalents of a saturated solution of fumaric acid in ethanol. The solution was concentrated to 10 ml and boiled briefly with 100 ml of ethyl acetate. There were obtained 1.7 g (57%) of 6-(m-chlorophenyl)-1,2,3,4-tetrahydro-1-methylpyrrolo[1,2-a]pyrazine fumarate (1:1); m.pt.: 165°–167° C. (dec.).

EXAMPLE 21

6-(p-Chlorophenyl)-3,4-dihydro-1-methylpyrrolo[1,2-a]pyrazine (1.0 g) was dissolved in a mixture of 100 ml of methanol and 10 ml of water under argon. The solution was treated portionwise with 0.5 g of sodium borohydride while stirring and stirred at room temperature overnight. Thereafter, the methanol was removed in a vacuum, the residue was taken up in 100 ml of methylene chloride and washed with 50 ml of 10% ammonia solution. The phases were separated and the aqueous phase was extracted twice with 70 ml of methylene chloride each time. The organic phases were combined, dried with MgSO₄ and freed from solvent. The crude product, 1.1 g of brown oil, was dissolved in a 30-fold amount of ethanol with the addition of a 5-fold amount of methylene chloride and treated with 1.1 equivalents of a saturated solution of fumaric acid in ethanol. There were obtained 1.1 g (74%) of 6-(p-chlorophenyl)-1,2,3,4-tetrahydro-1-methylpyrrolo[1,2-a]pyrazine fumarate (1:1); m.pt.: 196°–198° C. (dec.)

EXAMPLE 22

3,4-Dihydro-6-(p-methoxyphenyl)-1-methylpyrrolo[1,2-a]pyrazine (1.0 g) was dissolved in a mixture of 60 ml of methanol and 6 ml of water under argon. The solution was treated portionwise with 0.5 g of sodium borohydride while stirring and stirred at room temperature overnight. Thereafter, the methanol was removed in a vacuum, the residue was taken up in 100 ml of methylene chloride and washed with 45 ml of 10% ammonia solution. The phases were separated and the aqueous phase was extracted twice with 50 ml of methylene chloride each time. The organic phases were combined, dried with MgSO₄ and freed from solvent. The crude product, 1.0 g of brown solid, was dissolved in a 30-fold amount of ethanol and treated with 1.1 equivalents of a saturated solution of fumaric acid in ethanol. There was obtained 0.7 g (47%) of 1,2,3,4-tetrahydro-6-(p-methoxyphenyl)-1-methylpyrrolo[1,2-a]pyrazine fumarate (1:0.9); m.pt.: 162°–165° C. (dec.).

EXAMPLE 23

3,4-Dihydro-1-methyl-6-[4-(trifluoromethyl)phenyl]pyrrolo[1,2-a]pyrazine (2.5 g) was dissolved in a mixture of 130 ml of methanol and 13 ml of water under argon. The solution was treated portionwise with 1.0 g of sodium borohydride while stirring and stirred at room temperature overnight. Thereafter, the methanol was removed in a vacuum, the residue was taken up in 100 ml of methylene chloride and washed with 80 ml of 10% ammonia solution. The phases were separated and the aqueous phase was extracted twice with 50 ml of methylene chloride each time. The organic phases were combined, dried with MgSO₄ and freed from solvent. The crude product, 2.5 g of yellow-brown solid, was dissolved in a 20-fold amount of ethanol, treated with 1.1 equivalents of a saturated solution of fumaric acid in ethanol and concentrated to 40 ml. There were obtained 2.5 g (70%) of 1,2,3,4-tetrahydro-1-methyl-6-[4-(trifluoromethyl)phenyl]pyrrolo[1,2-a]pyrazine fumarate (1:1); m.pt.: 180°–183° C. (dec.).

EXAMPLE 24

6-(3,4-Dichlorophenyl)-3,4-dihydro-1-methylpyrrolo[1,2-a]pyrazine (1.8 g) was dissolved in a mixture of 100 ml of methanol and 10 ml of water under argon. The solution was treated portionwise with 0.7 g of sodium borohydride while stirring and stirred at room temperature overnight. Thereafter, the methanol was removed in a vacuum, the residue was taken up in 150 ml of methylene chloride and washed with 65 ml of 10% ammonia solution. The phases were separated and the aqueous phase was extracted twice with 70 ml of methylene chloride each time. The organic phases were combined, dried with MgSO₄ and freed from solvent. The crude product, 1.8 g of brown oil, was dissolved in a 20-fold amount of ethanol and treated with 1.1 equivalents of a saturated solution of fumaric acid in ethanol. There were obtained 2.0 g (92%) of 6-(3,4-dichlorophenyl)-1,2,3,4-tetrahydro-1-methylpyrrolo[1,2-a]pyrazine fumarate (2:1); m.pt.: 224°–226° C. (dec.).

EXAMPLE 25

3,4-Dihydro-1-methyl-6-p-tolylpyrrolo[1,2-a]pyrazine (1.8 g) was dissolved in a mixture of 100 ml of methanol and 10 ml of water under argon. The solution was treated portionwise with 0.9 g of sodium borohydride while stirring and stirred at room temperature overnight. Thereafter, the methanol was removed in a vacuum, the residue was taken up in 150 ml of methylene chloride and washed with 100 ml of 10% ammonia solution. The phases were separated and the aqueous phase was extracted twice with 70 ml of methylene chloride each time. The organic phases were combined, dried with MgSO$_4$ and freed from solvent. The crude product, 1.7 g of brown oil, was dissolved in a 25-fold amount of hot ethanol and treated with 1.1 equivalents of a hot, saturated solution of fumaric acid in ethanol. There were obtained 2.1 g (79%) of 1,2,3,4-tetrahydro-1-methyl-6-p-tolylpyrrolo[1,2-a]pyrazine fumarate (1:1); m.pt.: 196°–198° C. (dec.).

EXAMPLE 26

6-(3,4-Dimethoxyphenyl)-3,4-dihydro-1-methylpyrrolo[1,2-a]pyrazine (1.3 g) was dissolved in a mixture of 80 ml of methanol and 8 ml of water under argon. The solution was treated portionwise with 0.6 g of sodium borohydride while stirring and stirred at room temperature overnight. Thereafter, the methanol was removed in a vacuum, the residue was taken up in 100 ml of methylene chloride and washed with 100 ml of 10% ammonia solution. The phases were separated and the aqueous phase was extracted twice with 50 ml of methylene chloride each time. The organic phases were combined, dried with MgSO$_4$ and freed from solvent. The crude product, 1.3 g of yellow-brown oil, was chromatographed on 60 g of silica gel with methylene chloride/methanol (49:1) as the eluent. The product, 0.9 g of yellow oil was dissolved in a 20-fold amount of ethanol, treated with 1.1 equivalents of a saturated solution of fumaric acid in ethanol, concentrated to 10 ml and treated with 40 ml of ethyl acetate. There was obtained 0.5 g (37%) of 6-(3,4-dimethoxyphenyl)-1,2,3,4-tetrahydro-1-methylpyrrolo[1,2-a]pyrazine fumarate (1:0.6); m.pt.: 172°–175° C. (dec.). A sample was recrystallized from a 40-fold amount of ethanol and yielded the (2:1) fumarate; m.pt.: 178°–180° C. (dec.).

EXAMPLE 27

Crude 6-[p-(benzyloxy)phenyl]-3,4-dihydro-1-methylpyrrolo[1,2-]pyrazine (2.8 g) was dissolved in a mixture of 150 ml of methanol, 15 ml of water and 25 ml of methylene chloride under argon. The solution was treated portionwise with 1.0 g of sodium borohydride while stirring and stirred at room temperature overnight. Thereafter, the solvent was removed in a vaccum, the residue was taken up in 150 ml of methylene chloride and stirred at room temperature with 100 ml of 10% ammonia solution for ½ hour. The phases were separated and the aqueous phase was extracted twice with 70 ml of methylene chloride each time. The organic phases were combined, dried with MgSO$_4$ and freed from solvent. The crude product, 2.7 g of brown oil, was chromatographed on 60 g of silica gel with methylene chloride/methanol (49:1) as the eluent. The product, 1.0 g of beige coloured solid, was dissolved while heating in a 35-fold amount of ethanol and a 5-fold amount of methylene chloride and treated with 1.1 equivalents of a saturated solution of fumaric acid in ethanol. There was obtained 0.8 g (24%) of 6-[p-(benzyloxy)phenyl]-1,2,3,4-tetrahydro-1-methylpyrrolo[1,2-a]pyrazine fumarate (2:1); m.pt.: 172°–174° C. (dec.).

EXAMPLE 28

6-[p-(Cyclopentyloxy)phenyl]-3,4-dihydro-1-methylpyrrolo[1,2-a]pyrazine (1.5 g) was dissolved in a mixture of 100 ml of methanol, 10 ml of water and 25 ml of methylene chloride under argon. The solution was treated portionwise with 0.6 g of sodium borohydride while stirring and stirred at room temperature overnight. Thereafter, the solvent was removed in a vacuum, the residue was taken up in 100 ml of methylene chloride and washed with 100 ml of 10% ammonia solution. The phases were separated and the aqueous phase was extracted twice with 60 ml of methylene chloride each time. The organic phases were combined, dried with MgSO$_4$ and freed from solvent. The crude product, 1.6 g of brown oil, was dissolved in a 20-fold amount of hot ethanol and treated while hot with 1.1 equivalents of a saturated solution of fumaric acid in ethanol. There was obtained 1.2 g (66%) of 6-[p-(cyclopentyloxy)phenyl]-1,2,3,4-tetrahydro-1-methylpyrrolo[1,2-a]pyrazine fumarate (2:1); m.pt.: 172°–174° C. (dec.).

EXAMPLE 29

5,6,10,11-Tetrahydro-8-methylbenzo[g]pyrazino[1,2-a]indole (0.6 g) was dissolved in a mixture of 25 ml of ethanol and 2.5 ml of water under argon. The solution was treated portionwise with 0.3 g of sodium borohydride while stirring and stirred at room temperature overnight. Thereafter, the solvent was removed in a vacuum, the residue was taken up in 50 ml of methylene chloride and washed with 50 ml of 10% ammonia solution. The phases were separated and the aqueous phase was extracted twice with 20 ml of methylene chloride each time. The organic phases were combined, dried with MgSO$_4$ and freed from solvent. The crude product, 0.5 g of brown solid, was dissolved in a 20-fold amount of ethanol and treated with 1.1 equivalents of a saturated solution of fumaric acid in ethanol. There was obtained 0.2 g (24%) of 5,6,8,9,10,11-hexahydro-8-methylbenzo[g]pyrazino[1,2-a]indole fumarate (1:1); m.pt.: 181°–184° C. (dec.).

EXAMPLE 30

4-Chloro-5,6,10,11-tetrahydro-8-methylbenzo[g-]pyrazin[1,2-a]indole (2.1 g) was dissolved in a mixture of 70 ml of methanol and 7 ml of water under argon. The solution was treated portionwise with 0.9 g of sodium borohydride while stirring and stirred at room temperature overnight. Thereafter, the solvent was removed in a vacuum, the residue was taken up in 70 ml of methylene chloride and washed with 100 ml of 10% ammonia solution. The phases were separated and the aqueous phase was extracted twice with 40 ml of methylene chloride each time. The organic phases were combined, dried with MgSO$_4$ and freed from solvent. The crude product, 1.9 g of yellow, amorphous material, was dissolved in a 20-fold amount of hot ethanol and treated while hot with 1.1 equivalents of a saturated solution of fumaric acid in ethanol. There were obtained 2.3 g (78%) of 4-chloro-5,6,8,9,10,11-hexahydro-8-methylbenzo[g]pyrazino[1,2-a]indole fumarate (1:1); m.pt.: 199° C. (dec.).

EXAMPLE 31

3-Chloro-5,6,10,11-tetrahydro-8-methylbenzo[g]pyrazino[1,2-a]indole (0.9 g) was dissolved in a mixture of 40 ml of methanol and 4 ml of water under argon. The solution was treated portionwise with 0.4 g of sodium borohydride while stirring and stirred at room temperature overnight. Thereafter, the solvent was removed in a vacuum, the residue was taken up in 50 ml of methylene chloride and washed with 50 ml of 10% ammonia solution. The phases were separated and the aqueous phase was extracted twice with 30 ml of methylene chloride each time. The organic phases were combined, dried with MgSO$_4$ and freed from solvent. The crude product, 0.9 g of orange solid, was dissolved in a 40-fold amount of hot ethanol and treated while hot with 1.1 equivalents of a saturated solution of fumaric acid in ethanol. There was obtained 1.0 g (78%) of 3-chloro-5,6,8,9,10,11-hexahydro-8-methylbenzo[g]pyrazino[1,2-a]indole fumarate (1:1); m.pt.: 202°–203° C. (dec.).

EXAMPLE 32

2-Chloro-5,6,10,11-tetrahydro-8-methylbenzo[g]pyrazino[1,2-a]indole (1.1 g) was dissolved in a mixture of 50 ml of methanol and 5 ml of water under argon. The solution was treated portionwise with 0.5 g of sodium borohydride while stirring and stirred at room temperature overnight. Thereafter, the solvent was removed in a vacuum, the residue was taken up in 50 ml of methylene chloride and washed with 50 ml of 10% ammonia solution. The phases were separated and the aqueous phase was extracted twice with 30 ml of methylene chloride each time. The organic phases were combined, dried with MgSO$_4$ and freed from solvent. The crude product, 1.1 g of yellow, amorphous solid, was dissolved in a 20-fold amount of hot ethanol and treated while hot with 1.1 equivalents of a saturated solution of fumaric acid in ethanol. The separated crystals were recrystallized from a 50-fold amount of ethanol. There was obtained 1.0 g (74%) of 2-chloro-5,6,8,9,10,11-hexahydro-8-methylbenzo[g]pyrazine[1,2-a]indole fumarate (2:1); m.pt.: 198°–200° C. (dec.).

EXAMPLE 33

5,6,10,11-Tetrahydro-5,8-dimethylbenzo[g]pyrazino[1,2-a]indole (2.0 g) was dissolved in a mixture of 80 ml of methanol and 8 ml of water under argon. The solution was treated portionwise with 0.9 g of sodium borohydride while stirring and stirred at room temperature overnight. Thereafter, the solvent was removed in a vacuum, the residue was taken up in 100 ml of methylene chloride and washed with 100 ml of 10% ammonia solution. The phases were separated and the aqueous phase was extracted twice with 50 ml of methylene chloride each time. The organic phases were combined, dried with MgSO$_4$ and freed from solvent. The crude product, 2.0 g of yellow-brown oil, was dissolved in a 25-fold amount of hot ethanol and treated with 1.1 equivalents of a hot saturated solution of fumaric acid in ethanol. There were obtained 2.4 g (81%) of 5,6,8,9,10,11-hexahydro-5,8-dimethylbenzo[g]pyrazino[1,2-a]indole fumarate (1:1); m.pt.: 196°–199° C.

EXAMPLE 34 a) 3,4-Dihydro-1-methyl-6-phenylpyrrolo[1,2-a]pyrazine (0.6 g) was dissolved in 10 ml of ethanol and treated with 0.9 ml of methyl iodide under argon. The solution was boiled overnight, cooled and the separated crystals were filtered off. There was obtained 0.8 g (78%) of 3,4-dihydro-1,2-dimethyl-6-phenylpyrrolo[1,2-a]pyrazinium iodide; m.pt.: 213°–216° C. (dec.).

b) 3,4-Dihydro-1,2-dimethyl-6-phenylpyrrolo[1,2-a]pyrazinium iodide (0.4 g) was dissolved in 20 ml of methanol and 0.5 ml of water under argon and, after the addition of 0.2 g of sodium borohydride, stirred at room temperature for 15 minutes. The methanol was removed in a vacuum and the residue was stirred briefly with 50 ml of methylene chloride and 20 ml of 10% ammonia solution. The aqueous phase was extracted twice with 20 ml of methylene chloride each time, the organic phases were combined, dried with MgSO$_4$ and freed from solvent. The crude product, 0.2 g of yellow oil, was taken up in a 25-fold amount of ethanol, treated with 2 equivalents of a saturated solution of fumaric acid in ethanol, concentrated to 2 ml and boiled with 5 ml of ethyl acetate. There was obtained 0.2 g (51%) of 1,2,3,4-tetrahydro-1,2-dimethyl-6-phenylpyrrolo[1,2-a]pyrazine fumarate (1:1); m.pt. 127°–128° C. (dec.).

EXAMPLE 35

3,4-Dihydro-6-(p-methoxyphenyl)-1-methylpyrrolo[1,2-a]pyrazine (20.9 g) was boiled with 500 ml of 48% hydrobromic acid in an argon atmosphere while stirring for 1½ hours. The hydrobromic acid was removed in a vacuum and the residue was dissolved in 900 ml of ethyl acetate with the addition of 100 ml of methanol. The solution was stirred for 15 minutes with a mixture of 500 ml of saturated sodium hydrogen carbonate solution and 100 ml of 2N sodium hydroxide solution. The aqueous phase was brought to a pH value of 8–9 with 2N hydrochloric acid and extracted four times with 500 ml of an ethyl acetate/methanol mixture (9:1) each time. The aqueous phase was neutralized (pH=7) with 2N hydrochloric acid and continuously extracted overnight with 1000 ml of ethyl acetate. The organic phases were filtered, combined and concentrated to 150 ml. Then, 150 ml of ethyl acetate were added, the suspension was boiled and stored in a refrigerator overnight. 16.3 g of crude product were filtered off. 1.6 g thereof were dissolved in a 50-fold amount of methanol and a 10-fold amount of methylene chloride and treated with 1.1 equivalents of fumaric acid in 20 ml of methanol. There were obtained 1.8 g (62%) of 3,4-dihydro-6-(4-hydroxyphenyl)-1-methylpyrrolo[1,2-a]pyrazine fumarate (1:1); m.pt.: 209°–213° C. (dec.).

EXAMPLE 36

3,4-Dihydro-6-(4-hydroxyphenyl)-1-methylpyrrolo[1,2-a]pyrazine (5.0 g), 100 ml of methylene chloride, 5.3 ml of benzyl bromide and 0.8 g of benzyltributylammonium bromide was added in succession to a solution of 1.8 g of sodium hydroxide in 100 ml of water under argon. The mixture was boiled under reflux overnight and stirred and subsequently cooled. After the addition of 100 ml of methylene chloride and 100 ml of water the phases were separated and the aqueous phase was extracted twice with 100 ml of methylene chloride each time. The organic phases were combined, dried with MgSO$_4$ and freed from solvent. The residue, 10.3 g of brown oil, was chromatographed on 500 g of silica gel with methylene chloride/methanol mixtures (99:1 to 9:1) as the eluent. The crude product, 4.9 g of brown, amorphous material, was dissolved in a 10-fold amount of hot ethanol and treated with 1.1 equivalents of a saturated solution of fumaric acid in ethanol. The product, 2.2 g of yellow crystals, was recrystallized from a 20-fold amount of ethanol. There were obtained 1.8 g (19%) of 6-[p-(benzyloxy)phenyl]-3,4-dihydro-1-methylpyrrolo[1,2-a]pyrazine fumarate (1:1); m.pt.: 165°–168° C. (dec.).

EXAMPLE 37

Potassium carbonate (5.3 g) and 4.1 ml of bromocyclo-pentane was added in succession while stirring and under argon to a solution of 4.3 g of 3,4-dihydro-6-(4-hydroxyphenyl)-1-methylpyrrolo[1,2-a]pyrazine in 80 ml of dimethylformamide. The mixture was stirred at 80° C. for 65 hours, then at 100° C. for 24 hours and subsequently cooled. After the addition of 600 ml of water the mixture was extracted three times with 250 ml of ethyl acetate each time. The organic phases were washed with 300 ml of a mixture of water and saturated sodium chloride solution (1:1), combined, dried over MgSO4 and freed from solvent. The residue, 5.3 g of brown oil, was chromatographed on 150 g of silica gel with methylene chloride/methanol mixtures (49:1 to 24:1) as the eluent. 1.5 g of a total of 3.0 g of crude product were dissolved in a 30-fold amount of hot ethanol and treated with 1.1 equivalents of a hot saturated solution of fumaric acid in ethanol. After the addition of 30 ml of ethyl acetate there crystallized 1.4 g (36%) of 6-[p-(cyclopentyloxy)phenyl]-3,4-dihydro-1-methyl-pyrrolo[1,2-a]pyrazine fumarate (1:1); m.pt.: 155°–157° C. (dec.).

EXAMPLE 38 a) 1,2-Diphenylethanone (E/Z)-dimethylhydrazone (45.7 g) was dissolved in 500 ml of absolute tetrahydrofuran under argon and treated with 34.5 ml of N,N,N',N'-tetramethylethylenediamine. The reaction solution was cooled to −70° C. and 125 ml of a 1.6N solution of n-butyllithium in hexane were added dropwise within 30 minutes while stirring. The mixture was stirred at −70° C. for a further 30 minutes and then 27.1 ml of bromoacetaldehyde dimethyl acetal were then added dropwise at −30° C. Subsequently, the mixture was stirred at −30° C. for 2 hours and at room temperature for 16 hours. The reaction mixture was hydrolyzed with 500 ml of water and extracted twice with 250 ml of ethyl acetate. The combined organic extracts were dried over MgSO4 and freed from solvent. The crude product, 71 g of yellow oil, was distilled. There were obtained 20.9 g (33%) of 4,4-dimethoxy-1,2-diphenyl-1-butanone (E/Z)-dimethylhydrazone; b.p.: 114°–116° C./0.03 mbar.

b) 4,4-Dimethoxy-1,2-diphenyl-1-butanone (E/Z)-dimethylhydrazone (18.5 g) was dissolved in 125 ml of tetrahydrofuran and the resulting solution treated with 250 ml of 2N hydrochloric acid solution at room temperature while stirring and under argon and the mixture was stirred at room temperature overnight. The reaction mixture was extracted once with 400 ml of methylene chloride and twice with 200 ml of methylene chloride each time. The organic extracts were combined, dried with MgSO4 and freed from solvent. The residue, 15.2 g of yellow oil, was dissolved in 60 ml of acetic acid without further purification and added under argon and while stirring to a solution of 6.5 g of N-acetylethylenediamine in 40 ml of acetic acid. After the addition of 350 ml of ethanol the reaction solution was stirred at room temperature for 1 hour and subsequently the solvent and acetic acid were removed in a vacuum. The residue was taken up in 250 ml of methylene chloride and washed with a mixture of 250 ml of saturated sodium hydrogen carbonate solution and 130 ml of 2N sodium hydroxide solution. The aqueous phase was back-extracted three times with 100 ml of methylene chloride each time. The organic phases were combined, dried with MgSO4 and freed from solvent. The residue, 16.8 g of brown oil, was chromatographed on 500 g of silica gel with ethyl acetate/hexane (2:1) or ethyl acetate as the eluent. 5.8 g (30%) of N-[2-[2,3-diphenylpyrrol-1-yl]ethyl]acetamide were isolated as a pale yellow, amorphous solid. MS: m/e=304 (M+).

c) N-[2-[2,3-Diphenylpyrrol-1-yl]ethyl]acetamide (5.8 g) was treated with 25 ml of phosphorus oxychloride under argon and boiled under reflux for 1 hour. The reaction mixture was hydrolyzed at 0° C. with 100 ml of 2N sodium hydroxide solution and 150 ml of 28% sodium hydroxide solution, diluted with 1500 ml of water and extracted with methylene chloride (1×300 ml, 3×150 ml). The organic extracts were combined, washed once with 100 ml of saturated sodium chloride solution, dried with MgSO4 and freed from solvent. 3.5 g of a total of 5.5 g of crude product were dissolved in a 25-fold amount of ethanol and treated with 1.1 equivalents of a saturated solution of fumaric acid in ethanol. After the addition of 50 ml of ethyl acetate 3.6 (74%) of 3,4-dihydro-6,7-diphenyl-1-methylpyrrolo[1,2-a]pyrazine fumarate (1:1); m.pt.: 168°–170° C. (dec.).

EXAMPLE 39

3,4-Dihydro-6,7-diphenyl-1-methylpyrrolo[1,2-a]pyrazine (2.0 g) was dissolved in a mixture of 100 ml of methanol and 10 ml of water under argon. The solution was treated portionwise with 0.8 g of sodium borohydride while stirring and stirred at room temperature overnight. Thereafter, the methanol was removed in a vacuum, the residue was taken up in 150 ml of methylene chloride and washed with 100 ml of 10% ammonia solution. The phases were separated and the aqueous phase was extracted twice with 60 ml of methylene chloride each time. The organic phases were combined, dried with MgSO4 and freed from solvent. The crude produce, 2.0 g of yellow resin, was dissolved in a 20-fold amount of ethanol and boiled briefly with 1.1 equivalents of a saturated solution of fumaric acid in ethanol. There were obtained 2.1 g (86%) of 6,7-diphenyl-1,2,3,4-tetrahydro-1-methylpyrrolo[1,2-a]pyrazine fumarate (2:1); m.pt.: 187°–190° C. (dec.).

EXAMPLE 40 a) A 1.6N solution of n-butyllithium in n-hexane was added dropwise within 15 minutes at −70° C. under argon and while stirring to a solution of 7.1 ml of diisopropylamine in 200 ml of absolute tetrahydrofuran. The reaction mixture was stirred at 0° C. for 15 minutes, then again cooled to −70° C., treated with 30 ml of hexamethylphosphoric acid triamide and 9.5 g of 3-(1,3-dioxolan-2-yl)propiophenone, dissolved in 10 ml of absolute tetrahydrofuran and stirred for 15 minutes. After the addition of 3.2 ml of methyl iodide at −70° C. the mixture was brought to room temperature and stirred for 2 hours. The reaction solution was poured on to 100 ml of saturated ammonium chloride solution and extracted once with 200 ml of ethyl acetate and twice with 150 ml of ethyl acetate each time. The organic phases were washed with 100 ml of water, combined, dried with MgSO4 and filtered. The filtrate was concentrated and the residue, 23.4 g of brown oil, was chromatographed on 750 g of silica gel with hexane/ethyl acetate mixtures (4:1 to 2:1). 7.1 g (70%) of 3-(1,3-dioxolan-2-yl)-2-methylpropiophenone were isolated as a yellow oil.

b) 3-(1,3-Dioxolan-2-yl)-2-methylpropiophenone (7.1 g) was added to a solution of 6.6 g of N-acetylethylenediamine in 100 ml of acetic acid under argon and while stirring. The reaction solution was boiled for 18 hours and the acetic acid was subsequently removed in a vacuum. The residue was taken up in 200 ml of methylene chloride and washed with a mixture of 100 ml of saturated sodium hydrogen carbonate solution and 160 ml of 2N sodium hydroxide solution. The aqueous phase was back-extracted twice with 100 ml of methylene chloride each time. The organic phases were combined, dried with MgSO$_4$ and freed from solvent. The residue, 7.6 g of brown oil was chromatographed on 350 g of silica gel with ethyl acetate/hexane mixtures (1:3 to 2:1) as the eluent. 4.6 g (59%) of N-[2-[3-methyl-2-phenylpyrrol-1-yl]ethyl]acetamide were isolated as a brown, amorphous solid. MS: m/e=242 (M+).

c) N-[2-[3-Methyl-2-phenylpyrrol-1-yl]ethyl]acetamide (2.6 g) was treated with 20 ml of phosphorus oxychloride under argon and boiled under reflux for 1 hour. the reaction mixture was hydrolyzed at 0° C. with 100 ml of 2N sodium hydroxide solution and 100 ml of 28% sodium hydroxide solution, diluted with 1000 ml of water and extracted with methylene chloride (1×300 ml, 2×150 ml). The organic extracts were combined, washed once with 100 ml of water, dried with MgSO$_4$ and freed from solvent. 2.1 g of crude product were dissolved in a 25-fold amount of ethanol at the boiling temperature and treated with 1.1 equivalents of a saturated solution of fumaric acid in ethanol. After the addition of 50 ml of ethyl acetate 2.0 g of pale yellow crystals separated and were recrystallized from ethyl acetate/ethanol (1:1). There were obtained 1.3 g (30%) of 3,4-dihydro-1,7-dimethyl-6-phenylpyrrolo[1,2-a]pyrazine fumarate (2:3); m.pt.: 157°–159° C. (dec.).

EXAMPLE 41

3,4-Dihydro-1,7-dimethyl-6-phenylpyrrolo[1,2-a]pyrazine (0.6 g) was dissolved in a mixture of 40 ml of methanol and 4 ml of water under argon. The solution was treated portionwise with 0.3 g of sodium borohydride while stirring and stirred at room temperature overnight. Thereafter, the methanol was removed in a vacuum, the residue was taken up in 50 ml of methylene chloride and washed with 50 ml of 10% ammonia solution. The phases were separated and the aqueous phase was extracted twice with 30 ml of methylene chloride each time. The organic phases were combined, dried with MgSO$_4$ and freed from solvent. The crude product, 0.6 g of yellow, amorphous solid, was dissolved in a 25-fold amount of ethanol and treated with 1.1 equivalents of a saturated solution of fumaric acid in ethanol. There was obtained 0.5 g (63%) of 1,2,3,4-tetrahydro-1,7-dimethyl-6-phenylpyrrolo[1,2-a]pyrazine fumarate (2:1); m.pt.: 152°–154° C. (dec.).

EXAMPLE 42 a) 3-Phenylfuran (4.2 g) was dissolved in 100 ml of absolute tetrahydrofuran under argon and treated portionwise with 5.2 g of N-bromosuccinimide while stirring. After stirring at room temperature for 2 hours the solution was treated with a further 0.2 g of N-bromosuccinimide and stirred for a further 1 hour. Subsequently, the solution was concentrated to about 20 ml, treated with 100 ml of pentane and the separated succinimide was filtered off. The filtrate was washed twice with 100 ml of 1% sodium hydrogen carbonate solution each time and subsequently dried with Na$_2$SO$_4$ with the addition of a small amount of calcium carbonate and hydroquinone. The mixture was filtered, concentrated to 10 ml and made up to 100 ml with absolute tetrahydrofuran. This solution, without further purification, was cooled to −78° C. under argon, treated with 8.7 ml of N,N,N',N'-tetramethylethylenediamine and 37 ml of a 1.6N solution of n-butyllithium in hexane while stirring and stirred at −78° C. for 1 hour. Then, 3.1 ml of methyliodide were added dropwise between −50° C. and −30° C. and the solution was stirred at −20° C. for 30 minutes. Working-up was by the addition of 100 ml of saturated ammonium chloride solution and 40 ml of water. The mixture was extracted three times with 100 ml of ethyl acetate each time, the organic phases were combined, dried with MgSO$_4$, filtered and concentrated. The residue, 4.6 g of brown oil, was chromatographed on 100 g of aluminium oxide (neutral, III) with hexane as the eluent. 4.0 g of yellowish oil were isolated and were dissolved in 80 ml of dry acetonitrile under argon and stirred at room temperature for 4 hours with 7.9 g of the mixed anhydride from acetic acid and p-toluenesulphonic acid. Subsequently, the mixture was stirred for 30 minutes with 150 ml of saturated sodium hydrogen carbonate solution and 150 ml of diethyl ether. The phases were separated and the aqueous phase was extracted twice with a further 100 ml of diethyl ether. The organic phases were combined, washed twice with 50 ml of water each time, dried over MgSO$_4$ and freed from solvent. The residue, 4.2 of brown oil, was chromatographed on 200 g of silica gel with diethyl ether/hexane (1:5) as the eluent. 1.9 g (18%) of 2-acetyl-5-methyl-4-phenylfuran were obtained. MS: (m/e)=200 (M+).

b) 2-Acetyl-5-methyl-4-phenylfuran (1.9 g) was heated to 150° C. for 1 hour under argon with 6.3 ml of 1,2-ethanediamine and 0.6 ml of water. After cooling the mixture was poured into 500 ml of water and the mixture was extracted three times with 80 ml of methylene chloride each time. The organic phases were combined, dried with MgSO$_4$ and freed from solvent. The residue, 1.9 g of brown oil, was chromatographed on 100 g of aluminium oxide (neutral, III) with methylene chloride as the eluent. 0.6 g of a total of 1.2 g (56%) of crude product were dissolved in a 20-fold amount of ethanol and treated with 1.1 equivalents of a saturated solution of fumaric acid in ethanol. There was obtained 0.4 g of 3,4-dihydro-1,6-dimethyl-7-phenylpyrrolo[1,2-a]pyrazine fumarate (1:1); m.pt: 180°–182° C. (dec.).

EXAMPLE 43

3,4-Dihydro-1,6-dimethyl-7-phenylpyrrolo[1,2-a]pyrazine (0.5 g) was dissolved in a mixture of 20 ml of methanol and 2 ml of water under argon. The solution was treated portionwise with 0.25 g of sodium borohydride while stirring and stirred at room temperature overnight. Thereafter, the methanol was removed in a vacuum, the residue was taken up in 50 ml of methylene chloride and washed with 50 ml of 10% ammonia solution. The phases were separated and the aqueous phase was extracted twice with 30 ml of methylene chloride each time. The organic phases were combined, dried with MgSO$_4$ and freed from solvent. The crude product, 0.6 g of yellow oil, was dissolved in a 20-fold amount of ethanol and treated with 1.1 equivalents of a saturated solution of fumaric acid in ethanol. There was obtained 0.5 g (66%) of 1,2,3,4-tetrahydro-1,6-dimethyl-7-phenylpyrrolo[1,2-a]pyrazine fumarate (1:1); m.pt.: 196°-197° C. (dec.).

EXAMPLE 44

Diethyl azodicarboxylate (6.3 ml) was added at room temperature under argon and while stirring to a solution of 5.0 g of 3,4-dihydro-6-(4-hydroxyphenyl)-1-methyl-pyrrolo[1,2-a]pyrazine, 2.5 g of endo-norborneol and 8.7 g of triphenylphosphine in 250 ml of absolute tetrahydrofuran. The reaction mixture was boiled for 24 hours, cooled and treated with 100 ml of water. The mixture was extracted once with 200 ml of ethyl acetate and twice with 100 ml of ethyl acetate each time. The organic phases were washed twice with 100 ml of saturated sodium chloride solution each time, combined, dried with MgSO$_4$ and freed from solvent. The residue, 24.8 g of brown oil, was chromatographed on 500 g of silica gel with methylene chloride/methanol mixtures (100:1 to 10:1) as the eluent. 2.8 g of a total of 4.8 g of crude product were dissolved in a 20-fold amount of ethanol and treated with 1.1 equivalents of a saturated solution of fumaric acid in ethanol. After the addition of 50 ml of ethyl acetate there were obtained 3.1 g (55%) of 3,4-dihydro-1-methyl-6-[p-(2-exonobornyloxy)-phenyl]pyrrolo[1,2-a]pyrazine fumarate (1:1); m.pt.: 162°-163° C. (dec.).

EXAMPLE 45

3,4-Dihydro-1-methyl-6-[p-(2-exonorbornyloxy)-phenyl]pyrrolo[1,2-a]pyrazine (2.0 g) was dissolved in a mixture of 100 ml of methanol and 10 ml of water under argon. The solution was treated portionwise with 0.7 g of sodium borohydride while stirring and stirred at room temperature overnight. Thereafter, the methanol was removed in a vacuum, the residue was taken up in 100 ml of methylene chloride and washed with 100 ml of 10% ammonia solution. The phases were separated and the aqueous phase was extracted twice with 50 ml of methylene chloride each time. The organic phases were combined, dried with MgSO$_4$ and freed from solvent. The crude product, 1.6 g of amorphous, pink solid, was dissolved in a 20-fold amount of ethanol and treated with 1.1 equivalents of a saturated solution of fumaric acid in ethanol. There were obtained 1.2 g of pink coloured crystals which were recrystallized from 50 ml of ethanol. There was obtained 0.9 g (38%) of 1,2,3,4-tetrahydro-1-methyl-6-[p-(2-exonorbornyloxy)-phenyl]-pyrrolo[1,2-a]pyrazine fumarate (2:1); m.p.: 177°-180° C. (dec.).

EXAMPLE 46 a) N-[2-[2-(p-Methoxyphenyl)pyrrol-1-yl]ethyl]-acetamide (10.4 g) was dissolved in 300 ml of methylene chloride under argon, cooled to −15° C. and treated at this temperature while stirring with a solution of 11.6 ml of boron tribromide in 90 ml of methylene chloride. The mixture was stirred at −15° C. for 1 hour, at 0° C. for 2 hours and at room temperature overnight. The reaction mixture was treated at −10° C. with 270 ml of 2N sodium hydroxide solution and stirred at room temperature for 1 hour. 200 ml of methylene chloride were added to this mixture and the resulting mixture was adjusted to pH=8 with 70 ml of 2N hydrochloric acid. The phases were separated and the aqueous phase was extracted twice with 150 ml of methylene chloride each time. The organic phases were combined, dried with MgSO$_4$ and freed from solvent. The residue, 8.2 g of brown oil, was chromatographed on 250 g of silica gel with methylene chloride/methanol mixtures (50:1 to 20:1) as the eluent. There were obtained 5.4 g (55%) of N-[2-[2-(p-hydroxyphenyl)pyrrol-1-yl]ethyl]acetamide as a colourless, amorphous solid which was processed without further purification. MS: (m/e)=244 (M+).

b) N-[2-[2-(p-Hydroxyphenyl)pyrrol-1-yl]ethyl]acetamide (36.0 g) was dissolved in 350 ml of dioxan and 350 ml of water under argon and stirred at room temperature for 4 hours with 44 ml of benzyl chloroformate and 50 g of sodium hydrogen carbonate. Subsequently, 500 ml of ethyl acetate and 500 ml of water were added, the phases were separated and the aqueous phase was extracted twice with 300 ml of ethyl acetate each time. The organic extracts were washed once with 300 ml of saturated sodium chloride solution, combined, dried with MgSO$_4$ and freed from solvent, the residue, 80.1 g of brown oil, was taken up in 250 ml of ethyl acetate. There separated 35.0 g (63%) of carbonic acid benzyl ester 4-[1-(2-N-acetylamino-ethyl)pyrrol-2-yl]phenyl ester; m.pt.: 114°-117° C.

c) Carbonic acid benzyl ester 4-[1-(2-N-acetylamino-ethyl)pyrrol-2-yl]phenyl ester (6.4 g) was treated with 20 ml of phosphorus oxychloride under argon and the mixture was boiled for 30 minutes. The cooled mixture was added to 2500 g of ice-water and made strongly basic with 28% sodium hydroxide solution. The mixture was extracted four times with 200 ml of methylene chloride each time, the organic phases were combined, dried with MgSO$_4$ and freed from solvent. 0.8 g of a total of 6.2 g of crude product were dissolved in a 25-fold amount of hot ethanol and treated while hot with 1.1 equivalents of a saturated solution of fumaric acid in ethanol. There was obtained 0.7 g (67%) of carbonic acid benzyl ester 4-(3,4-dihydro-1-methylpyrrolo[1,2-a]pyrazin-6-yl)phenyl ester fumarate (1:1); m.pt.: 165°-167° C. (dec.).

EXAMPLE 47

3,4-Dihydro-6-(4-hydroxyphenyl)-1-methylpyrrolo[1,2-a]pyrazine (0.23 g) in 10 ml dimethylacetamide was cooled to 0° C. under argon. 42 mg of sodium hydride dispersion (60%) were added at this temperature while stirring and the mixture was stirred at 0° C. for half an hour. Subsequently, a solution of 0.36 g of N-phenyl-bis(trifluoromethanesulphonimide) in 3 ml of tetrahydrofuran was added dropwise within 5 minutes and the mixture was stirred at 0° C. for one hour. Subsequently, 20 ml of saturated ammonium chloride solution and 10 ml of water were added. The mixture was extracted twice with 25 ml of ethyl acetate each time, the organic phases were washed with 20 ml of 1N sodium carbonate solution and 30 ml of saturated sodium chloride solution, combined, dried with MgSO$_4$ and freed from solvent. The residue, 0.65 g of orange coloured oil, was chromatographed on 30 g of silica gel with methylene chloride/methanol mixtures (50:1 to 20:1). There was obtained 0.24 g of pale yellow oil which was dissolved in a 20-fold amount of ethanol and treated with 1.1 equivalents of a saturated solution of fumaric acid in ethanol. After the addition of 10 ml of ethyl acetate there was obtained 0.2 g (42%) of trifluoromethanesulphonic acid 4-(3,4-dihydro-1-methylpyrrolo[1,2-a]pyrazin-6-yl)phenyl ester fumarate (1:1); m.pt.: 146° C. (dec.).

EXAMPLE 48

Toluenesulphonic acid 3-hydroxybutan-1-yl ester (1.8 g) and 1.8 g of potassium carbonate was added at room temperature while stirring and under argon to a solution of 1.5 g of 3,4-dihydro-6-(4-hydroxyphenyl)-1-methylpyrrolo[1,2-a]pyrazine in 20 ml of 2-butanone and the mixture was boiled for 20 hours. The cooled reaction mixture was treated with 100 ml of 2N sodium hydroxide solution and extracted three times with 200 ml of methylene chloride each time. The organic phases were washed twice with 100 ml of water each time, combined, dried with MgSO$_4$ and freed from solvent. The residue, 2.4 g of brown oil, was chromatographed on 50 g of silica gel with methylene chloride/methanol mixtures (50:1 to 20:1) as the eluent. There were obtained 1.2 g of an orange coloured, amorphous solid which was dissolved in a 25-fold amount of ethanol and treated while hot with 1.1 equivalents of a saturated solution of fumaric acid in ethanol. There were obtained 1.5 g (90%) of 4-[4-(3,4-dihydro-1-methylpyrrolo[1,2-a]pyrazin-6-yl)phenoxy]butan-2-ol fumarate (1:1); m.pt.: 156°-157° C. (dec.).

EXAMPLE 49 a) 3,4-dihydro-6-methoxy-1(2H)-naphthalenone (198 g) was dissolved in 2000 ml of toluene under argon and treated in succession with 193 ml of 3-buten-2-ol, 206 ml of 2,2-dimethoxypropane and 1.9 g of p-toluenesulphonic acid. The reaction mixture was boiled at reflux for 20 hours, treated with a further 175 ml of 3-buten-2-ol and 180 ml of 2,2-dimethoxypropane and boiled for a further 50 hours. After cooling the solution was washed with 500 ml of saturated sodium hydrogen carbonate solution, the aqueous phase was extracted once with 600 ml of ethyl acetate, the organic phases were combined, dried with MgSO$_4$ and freed from solvent. The residue, 269 g of brown oil, was chromatographed on 3000 g of silica gel with hexane/diethyl ether (5:1) as the eluent. There were obtained 147 g (57%) of 2-(2-butenyl)-3,4-dihydro-6-methoxy-1(2H)-naphthalenone which was processed without further purification.

b) 2-(2-Butenyl)-3,4-dihydro-6-methoxy-1(2H)-naphthalenone (65.3 g) was dissolved in a mixture of 2000 ml of methylene chloride and 500 ml of methanol, cooled to −78° C. and ozonized. After completion of the reaction 29 ml of dimethyl sulphide were added at −78° C. and the mixture was brought to room temperature overnight. Subsequently, the solvent was removed. The residue, 97.2 g of orange coloured oil, was dissolved in 2000 ml of methylene chloride, treated with 400 g of silica gel and 80 ml of 10% oxalic acid and stirred at room temperature overnight under argon. The mixture was filtered and the filtrate was concentrated. The residue, 71.8 g of green oil, was dissolved in 400 ml of methylene chloride under argon without further purification, treated with 200 g of molecular sieve 4 Å and 37.1 g of N-acetylethylenediamine and boiled overnight. The reaction mixture was cooled, filtered over a Celite ® pad and the filtrate was freed from solvent. The residue, 98.0 g of brown, crystalline solid, was filtered over 1000 g of silica gel with ethyl acetate as the eluent and the filtrate was concentrated to a volume of 350 ml. There separated 48.4 g (60%) of N-[2-(4,5-dihydro-7-methoxy-1H-benzo[g]indol-1-yl)ethyl]acetamide; m.pt.: 134° C.

c) N-[2-(4,5-Dihydro-7-methoxy-1H-benzo[g]indol-1-yl)ethyl]acetamide (14.5 g) was treated with 50 ml of phosphorus oxychloride under argon and the mixture was stirred at 50° C. for 30 minutes. The cooled mixture was added to 5000 g of ice-water and treated with 500 ml of 28% sodium hydroxide solution. The mixture was extracted once with 1000 ml of methylene chloride and twice with 500 ml of methylene chloride each time, the organic phases were combined, dried with MgSO$_4$ and freed from solvent. The residue, 14.6 g of brown oil, was chromatographed on 220 g of aluminium oxide (neutral, III) with methylene chloride as the eluent. 1.3 g of a total of 10.3 g of crude product were dissolved in a 25-fold amount of ethanol and treated with 1.1 equivalents of a saturated solution of fumaric acid in ethanol. There were obtained 1.2 g (49%) of 5,6,10,11-tetrahydro-3-methoxy-8-methyl-benzo[g]pyrazino[1,2-a]indole fumarate (1:1); m.pt.: 202°-203° C. (dec.).

EXAMPLE 50 a) N-[2-(4,5-Dihydro-7-methoxy-1H-benzo[g]indol-3-yl)ethyl]acetamide (48.8 g) was dissolved in 1000 ml of methylene chloride under argon, cooled to −15° C. and treated at this temperature while stirring with a solution of 50 ml of borontribromide in 300 ml of methylene chloride. The mixture was stirred at −15° C. for 1 hour, at 0° C. for 5 hours at room temperature overnight. The reaction mixture was treated at −10° C. with 1000 ml of 2N sodium hydroxide solution and stirred at room temperature for 1 hour. 500 ml of methylene chloride were added to this mixture and the resulting mixture was adjusted to pH=8 with 250 ml of 2N hydrochloric acid. The phases were separated and the aqueous phase was extracted twice with 500 ml of methylene chloride each time. The organic phases were combined, dried with MgSO$_4$ and freed from solvent. The residue, 33.2 g of yellow-brown, amorphous material, was chromatographed on 500 g of silica gel with methylene chloride/methanol mixtures (50:1 to 20:1) as the eluent. There were obtained 30.2 g (65%) of N-[2-[4,5-dihydro-7-hydroxy-1H-benzo[g]indol-1-yl)ethyl]acetamide which was processed without further purification. MS: (m/e)=270 (M+).

b) N-[2-[4,5-Dihydro-7-hydroxy-1H-benzo[g]indol-1-yl)ethyl]acetamide (29.7 g) was dissolved in 300 ml of dioxan and 300 ml of water under argon and treated with 28.4 g of 4-nitrobenzyl chloroformate and 22.2 g of sodium hydrogen car- bonate and the mixture was stirred at room temperature overnight. Thereafter, a further 10.0 g of 4-nitrobenzyl chloroformate and 7.8 g of sodium hydrogen carbonate were added and the mixture was stirred at room temperature for a further 1 hour. Subsequently, 1000 ml of ethyl acetate and 500 ml of water were added, the phases were separated and the aqueous phase was extracted twice with 1000 ml of ethyl acetate each time. The organic extracts were combined, dried with MgSO$_4$ and concentrated to a volume of 300 ml. There separated 30.5 g (67%) of carbonic acid 1-(2-N-acetylamino-ethyl)-4,5-dihydro-1H-benzo[g]indol-7-yl ester 4-nitrobenzyl ester; m.pt.: 144°-148° C.

c) Carbonic acid 1-(2-N-acetylamino-ethyl)-4,5-dihydro-1H-benzo[g]indol-7-yl ester 4-nitrobenzyl ester (41.2 g) was treated with 100 ml of phosphorus oxychloride under argon and the mixture was heated to 50° C. for 30 minutes. The cooled mixture was added to 20 l of ice-water and treated with 700 ml of 28% sodium hydroxide solution. The mixture was extracted once with 3 l of methylene chloride and twice with 1 l of methylene chloride each time, the organic phases were combined, dried with MgSO$_4$ and freed from solvent. 1.5 g of a total of 39.2 g of crude product were dissolved in a 25-fold amount of hot ethanol and treated while hot with 1.1 equivalents of a saturated solution of fumaric acid in ethanol. There were obtained 1.5 g (78%) of carbonic acid 5,6,10,11-tetrahydro-8-methyl-benzo[g]pyrazino[1,2-a]indol-3-yl ester 4-nitrobenzyl ester fumarate (1:1); m.pt.: 175°-176° C. (dec.).

EXAMPLE 51

Carbonic acid 5,6,10,11-tetrahydro-8-methyl-benzo[g]pyrazino[1,2-a]indol-3-yl ester 4-nitrobenzyl ester (37.8 g) was dissolved in 800 ml of methylene chloride under argon and, after the addition of 75 ml of n-propylamine, stirred at room temperature overnight. The product separated in the form of 21.8 g (98%) of ochre-coloured crystals; m.pt.:>250° C. 0.4 g thereof was suspended in 20 ml of methanol and treated with 1 equivalent of methanesulphonic acid. After the addition of 50 ml of diethyl ether there separated 0.4 g of 5,6,10,11-tetrahydro-8-methyl-benzo[g]pyrazino[1,2-a]indol-3-ol methanesulphonate (1:1); m.pt.:>240° C.

EXAMPLE 52 a) N-[2-(4,5-Dihydro-5-methyl-1H-benzo[g]indol-1-yl)ethyl]acetamide (5.0 g) was suspended in 80 ml of toluene under argon, treated with 4.7 g of 2,3-dichloro-5,6-dicyano-1,4-benzoquinone and stirred at 80° C. for 4 hours. A further 1.0 g of 2,3-dichloro-5,6-dicyano-1,4-benzoquinone was added and the mixture was stirred at 80° C. for a further 1 hour. The solution was cooled and filtered over 60 g of aluminium oxide (neutral, III) with ethyl acetate as the eluent. The filtrate was concentrated and yielded 0.3 g (6%) of N-[2-(5-methyl-1H-benzo[g]indol-1-yl)ethyl]acetamide as an amorphous, yellow solid which was processed without further purification.

b) N-[2-(5-Methyl-1H-benzo[g]indol-1-yl)ethyl]acetamide (0.3 g) was treated with 3 ml of phosphorous oxychloride under argon and the mixture was heated to 100° C. for 30 minutes. The cooled mixture was added to 250 g of ice-water and treated with 30 ml of 28% sodium hydroxide solution. The mixture was extracted once with 100 ml of methylene chloride and twice with 50 ml of methylene chloride each time, the organic phases were combined, dried with MgSO$_4$ and freed from solvent. The residue, 0.14 g of brown oil, was chromatographed on 10 g of aluminium oxide (neutral, III) with methylene chloride as the eluent. The crude product, 90 mg of yellow-brown, amorphous solid was dissolved in 1 ml of ethanol and 3 ml of diethyl ether and treated with 1.1 equivalents of a saturated solution of fumaric acid in ethanol. There were obtained 58 mg (17%) of 10,11-dihydro-5,8-dimethylbenzo[g]pyrazino[1,2-a]indole fumarate (2:1); m.pt.: 184°-186° C. (dec.).

EXAMPLE 53

Diethyl azodicarboxylate (3.7 ml) was added at room temperature under argon and while stirring to a solution of 4.0 g of 5,6,10,11-tetrahydro-8-methyl-benzo[g]pyrazino[1,2-a]indol-3-ol, 1.5 ml of cyclopentanol and 6.2 g of triphenylphosphine in 250 ml of absolute tetrahydrofuran. The reaction mixture was boiled overnight and then treated with a further 2.0 g of triphenylphosphine and 1.2 ml of diethyl azodicarboxylate. The mixture was subsequently cooled and treated with 300 ml of water. The mixture was extracted once with 300 ml of ethyl acetate and twice with 250 ml of ethyl acetate each time. The organic phases were washed once with 250 ml of saturated sodium chloride solution, combined, dried with MgSO$_4$ and freed from solvent. The residue, 19.6 g of brown oil was chromatographed on 500 g of silica gel with methylene chloride/methanol mixtures (50:1 to 20:1) as the eluent. 1.2 g of a total of 2.0 g of crude product were dissolved in a 20-fold amount of ethanol and treated with 1.1 equivalents of a saturated solution of fumaric acid in ethanol. There separated 1.1 g (26%) of 3-cyclopentyloxy-5,6,10,11-tetrahydro-8-methylbenzo[g]pyrazino[1,2-a]indole fumarate (1:1); m.pt.: 182°-185° C. (dec.).

EXAMPLE 54

3-Cyclopentyloxy-5,6,10,11-tetrahydro-8-methylbenzo[g]pyrazino[1,2-a]indole (0.8 g) was dissolved in a mixture of 50 ml of methanol and 5 ml of water under argon. The solution was treated portionwise with 0.3 g of sodium borohydride while stirring and stirred at room temperature overnight. Thereafter, the methanol was removed in a vacuum, the residue was taken up in 30 ml of methylene chloride and washed with 50 ml of 10% ammonia solution. The phases were separated and the aqueous phase was extracted twice with 30 ml of methylene chloride each time. The organic phases were combined, dried with MgSO$_4$ and freed from solvent. The residue, 0.8 g of amorphous, brown solid, was chromatographed on 30 g of silica gel with methylene chloride/methanol mixtures (50:1 to 20:1). The isolated crude product was dissolved in a 25-fold amount of hot ethanol and treated with 1.1 equivalents of a saturated solution of fumaric acid in ethanol. There was obtained 0.34 g (31%) of 3-cyclopentyloxy-5,6,8,9,10,11-hexahydro-8-methyl-benzo[g]pyrazino[1,2-a]indole fumarate (2:1); m.pt.: 187°-189° C. (dec.).

EXAMPLE 55

Diethyl azodicarboxylate (1.9 ml) was added dropwise at room temperature under argon and while stirring to a solution of 2.0 g of 5,6,10,11-tetrahydro-8-methyl-benzo[g]pyrazino[1,2-a]indol-3-ol, 0.9 ml of cyclohexanol and 3.1 g of triphenylphosphine in 120 ml of absolute tetrahydrofuran. The reaction mixture was boiled overnight and then treated with a further 1.5 g of triphenylphosphine and 1.0 ml of diethyl azodicarboxylate and the mixture was again boiled overnight. Subsequently, it was cooled and treated with 150 ml of water. The mixture was extracted three times with 150 ml of ethyl acetate each time. The organic phases were washed once with 100 ml of saturated sodium chloride solution, combined, dried with MgSO$_4$ and freed from solvent. The residue, 9.9 g of brown oil, was chromatographed on 200 g of silica gel with methylene chloride/methanol mixtures (50:1 to 10:1) as the eluent. 0.54 g of crude product was dissolved in a 25-fold amount of ethanol and treated with 1.1 equivalents of a saturated solution of fumaric acid in ethanol. There separated 0.45 g (12%) of 3-cyclohexyloxy-5,6,10,11-tetrahydro-8-methylbenzo[g]pyrazino[1,2-a]indole fumarate (3:4); m.pt.: 199°-202° C. (dec.).

EXAMPLE 56

Diethyl azodicarboxylate (1.0 ml) was added dropwise at room temperature under argon and while stirring to a solution of 1.0 g of 5,6,10,11-tetrahydro-8-methyl-benzo[g]pyrazino[1,2-a]indol-3-ol, 0.3 ml of isopropanol and 1.6 g of triphenylphosphine in 60 ml of absolute tetrahydrofuran. The reaction mixture was boiled overnight and then treated with a further 0.3 ml of isopropanol, 1.5 g of triphenyl phosphine and 1.0 ml of diethyl azodicarboxylate and again boiled overnight. Subsequently, the mixture was cooled and treated with 80 ml of ethyl acetate. It was extracted three times with 30 ml of 2N hydrochloric acid each time. The aqueous phases were washed once with 80 ml of ethyl acetate, combined, made strongly basic with 28% sodium hydroxide solution and extracted three times with 60 ml of methylene chloride each time. The organic phases were combined, dried with MgSO$_4$ and freed from solvent. The residue, 1.1 g of brown oil, was chromatographed on 80 g of aluminium oxide (neutral, III) with methylene chloride as the eluent. 0.8 g of crude product was dissolved in a 20-fold amount of hot ethanol and treated with 1.1 equivalents of a saturated solution of fumaric acid in ethanol. After the addition of 40 ml of ethyl acetate there separated 0.55 g (34%) of 5,6,10,11-tetrahydro-3-isopropoxy-8-methyl-benzo[g]pyrazino[1,2-a]indole fumarate (1:1); m.pt.: 176°–177° C. (dec.).

EXAMPLE 57

Diethyl azodicarboxylate (1.0 ml) was added dropwise at room temperature under argon and while stirring to a solution of 1.0 g of 5,6,10,11-tetrahydro-8-methyl-benzo[g]pyrazino[1,2-a]indol-3-ol, 0.6 ml of n-octanol and 1.6 g of triphenylphosphine in 60 ml of absolute tetrahydrofuran. The reaction mixture was boiled overnight and subsequently cooled and treated with 100 ml of ethyl acetate. The mixture was extracted three times with 30 ml of 2N hydrochloric acid each time. The aqueous phases were extracted once with 60 ml of ethyl acetate. The organic phases were combined, dried with MgSO$_4$ and freed from solvent. The residue, 4.3 g of brown oil, was chromatographed on 200 g of aluminium oxide (neutral, III) with methylene chloride as the eluent and subsequently over 40 g of silica gel with methylene chloride/methanol mixtures (20:1 to 10:1). 0.5 g of crude product were dissolved in a 20-fold amount of ethanol and treated with 1.1 equivalents of a saturated solution of fumaric acid in ethanol. There separated 0.4 g (21%) of 5,6,10,11-tetrahydro-8-methyl-3-octyloxy-benzo[g]pyrazino[1,2-a]indole fumarate (1:1); m.pt.: 151°–152° C. (dec.).

EXAMPLE 58

Diethyl azodicarboxylate (1.0 ml) was added dropwise at room temperature under argon and while stirring to a solution of 1.0 g of 5,6,10,11-tetrahydro-8-methyl-benzo[g]pyrazino[1,2-a]indol-3-ol, 0.5 g of 4-(2-hydroxyethyl)morpholine and 1.6 g of triphenylphosphine in 60 ml of absolute tetrahydrofuran. The reaction mixture was boiled overnight and subsequently cooled and treated with 100 ml of ethyl acetate. The mixture was extracted three times with 50 ml of 2N hydrochloric acid each time. The aqueous phases were washed once with 60 ml of ethyl acetate, combined, made strongly basic with 28% sodium hydroxide solution and extracted three times with 60 ml of ethyl acetate each time. The organic phases were combined, dried with MgSO$_4$ and freed from solvent. The residue, 1.7 g of brown oil, was chromatographed on 40 g of silica gel with methylene chloride/methanol mixtures (100:1 to 10:1). 0.15 g of crude product was dissolved in a 20-fold amount of ethanol and treated with 1.1 equivalents of a saturated solution of fumaric acid in ethanol. There separated 0.11 g (5%) of 5,6,10,11-tetrahydro-8-methyl-3-(2-morpholin-4-yl-ethoxy)-benzo[g]pyrazino[1,2-a]indole fumarate (1:2); m.pt.: 195°–197° C. (dec.).

EXAMPLE 59

Diethyl azodicarboxylate (1.0 ml) was added dropwise at room temperature under argon and while stirring to a solution of 1.0 g of 5,6,10,11-tetrahydro-8-methyl-benzo[g]pyrazino[1,2-a]indol-3-ol, 0.45 ml of 1-(2-hydroxyethyl)-2-pyrrolidone and 1.6 g of triphenylphosphine in 60 ml of absolute tetrahydrofuran. The reaction mixture was boiled overnight and subsequently cooled and treated with 100 ml of ethyl acetate. The mixture was extracted three times with 30 ml of 2N hydrochloric acid each time. The aqueous phases were washed once with 80 ml of ethyl acetate, combined, made strongly basic with 28% sodium hydroxide solution and extracted three times with 60 ml of ethyl acetate each time. The organic phases were combined, dried with MgSO$_4$ and freed from solvent. The residue, 2.4 g of brown oil, was chromatographed on 150 g of aluminium oxide (neutral, III) with methylene chloride and methylene chloride/methanol (100:1) as the eluent. 1.0 g of crude product was dissolved in a 20-fold amount of ethanol and treated with 1.1 equivalents of a saturated solution of fumaric acid in ethanol. After the addition of 70 ml of ethyl acetate there separated 0.8 g (42%) of 1-[2-(5,6,10,11-tetrahydro-8-methyl-benzo[g]pyrazino[1,2-a]indol-3-yloxy)ethyl]pyrrolidin-2-one fumarate (1:1); m.pt.: 183°–185° C. (dec.).

EXAMPLE 60

Toluenesulphonic acid 3-hydroxybutan-1-yl ester (1.1 g) and 1.0 g of potassium carbonate was added at room temperature while stirring and under argon to a solution of 1.0 g of 5,6,10,11-tetrahydro-8-methyl-benzo[g]pyrazino[1,2-a]indole-3-ol in 20 ml of 2-butanone and the mixture was boiled overnight. The cooled reaction mixture was treated with 100 ml of 2N sodium hydroxide solution and extracted three times with 200 ml of methylene chloride each time. The organic phases were washed twice with 50 ml of sodium hydroxide solution each time, combined, dried with MgSO$_4$ and freed from solvent. The residue, 1.1 g of brown, amorphous material, was chromatographed on 80 g of aluminium oxide (neutral, III) with methylene chloride and methylene chloride/methanol (100:1) as eluents. There was obtained 0.8 g of a yellow oil which was dissolved in a 20-fold amount of ethanol and treated with 1.1 equivalents of a saturated solution of fumaric acid in ethanol. There was obtained 0.8 g (46%) of 4-(5,6,10,11-tetrahydro-8-methyl-benzo[g]pyrazino[1,2-a]indol-3-yloxy)butan-2-ol-fumarate (1:1); m.pt.: 180°–182° C. (dec.).

EXAMPLE 61

Isobutylene (11.0 g) was condensed under argon into a solution of 1.0 g of 5,6,10,11-tetrahydro-8-methyl-benzo[g]pyrazino[1,2-a]indol-3-ol in 50 ml of methylene chloride. The solution was cooled to −78° C. and treated with 0.4 ml of trifluoromethanesulphonic acid while stirring. The mixture was stirred at −78° C. for 8 hours and at −5° C. for 30 minutes. Subsequently, 50 ml of methanol were added and the mixture was neutralized with powdered sodium hydroxide. The reaction mixture was freed from solvent and chromatographed over 100 g of aluminium oxide (neutral, III) with methylene chloride as the eluent. The crude product, 0.3 g of yellow oil, was dissolved in a 20-fold amount of ethanol and treated with 1.1 equivalents of a saturated solution of fumaric acid in ethanol. The solution was concentrated to half and treated with 5 ml of ethyl acetate. There was obtained 0.11 g (6%) of 3-tert-butoxy-5,6,10,11-tetrahydro-8-methyl-benzo[g]pyrazino[1,2-a]indole fumarate (1:1); m.pt.: 179°-181° C. (dec.).

EXAMPLE 62

5,6,10,11-Tetrahydro-8-methyl-benzo[g]pyrazino[1,2-a]indol-3-ol (2.0 g) was dissolved in 200 ml of hot dimethylacetamide under argon and cooled to 0° C. 0.33 g of sodium hydride dispersion (60%) was added at this temperature while stirring and the mixture was stirred at 0° C. for 1 hour. Subsequently, a solution of 2.8 g of N-phenyl-bis-(trifluoromethanesulphonimide) in 25 ml of tetrahydrofuran was added dropwise within 10 minutes and the mixture was stirred at 0° C. for 1 hour. Subsequently, 400 ml of saturated ammonium chloride solution and 250 ml of water were added. The mixture was extracted three times with 200 ml of ethyl acetate each time, the organic phases were washed with 250 ml of water, 200 ml of 1N sodium carbonate solution and 200 ml of saturated sodium chloride solution, combined, dried with $MgSO_4$ and freed from solvent. The residue, 4.9 g of brown oil, was chromatographed on 250 g of silica gel with methylene chloride/methanol mixtures (50:1 to 20:1). There were obtained 2.1 g (69%) of trifluoromethane-sulphonic acid 5,6,10,11-tetrahydro-8-methyl-benzo[g]pyrazino[1,2-a]indol-3-yl ester. 0.5 g thereof was dissolved in a 20-fold amount of ethanol and treated with 1.1 equivalents of a saturated solution of fumaric acid in ethanol. There separated 0.4 g of trifluoromethanesulphonic acid 5,6,10,11-tetrahydro-8-methyl-benzo[g]pyrazino[1,2-a]indol-3-yl ester fumarate (1:1); m.pt.: 165°-167° C. (dec.).

EXAMPLE 63 a) 3,4-Dihydro-7-methoxy-1(2H)-naphthalenone (50.9 g) was suspended in 200 ml of ethanol under argon, treated with 44 ml of N,N-dimethylhydrazine (asym.) and boiled under reflux for 168 hours. The reaction mixture was freed from solvent and excess dimethylhydrazine in a vacuum. The residue was taken up in 400 ml of ethyl acetate and treated at 0° C. with 100 ml of 3.3N HCl in ethyl acetate. The mixture was stirred at 0° C. for 30 minutes, the separated crystals were filtered off and again suspended in ethyl acetate. 500 ml of saturated sodium hydrogen carbonate solution were added to this suspension and the mixture was stirred for 30 minutes. The phases were separated and the aqueous phase was extracted twice with ethyl acetate. The organic phases were combined, dried with $MgSO_4$ and freed from solvent. 56.8 g (90%) of 3,4-dihydro-7-methoxy-1(2H)-naphthalenone N',N'-dimethylhydrazone were processed without further purification.

b) 3,4-Dihydro-7-methoxy-1(2H)-naphthalenone N',N'-dimethylhydrazone (56.8 g) was dissolved in 1100 ml of absolute tetrahydrofuran under argon and treated with 47 ml of N,N,N',N'-tetramethylethylenediamine. The reaction solution was cooled to −70° C. and 170 ml of a 1.6N solution of n-butyllithium in hexane was added dropwise within 45 minutes while stirring. The mixture was stirred at −70° C. for a further 30 minutes and then 37 ml of bromoacetaldehyde dimethyl acetal were added dropwise at −30° C. within 15 minutes. Subsequently, the mixture was stirred at −30° C. for 2 hours and at room temperature for 16 hours. The reaction mixture was hydrolyzed with 1400 ml of water, extracted once with 1200 ml of ethyl acetate and twice with 800 ml of ethyl acetate each time. The combined organic extracts were dried over $MgSO_4$ and freed from solvent. The crude product was chromatographed on 2000 g of silica gel with hexane/ethyl acetate mixtures (4:1 to 2:1) as the eluent. There were obtained 46.6 g (59%) of 1,2,3,4-tetrahydro-1-(dimethylhydrazono)-7-methoxy-2-naphthaleneacetaldehyde dimethyl acetal.

c) 1,2,3,4-Tetrahydro-1-(dimethylhydrazono)-7-methoxy-2-naphthaleneacetaldehyde dimethyl acetal (45.0 g) was dissolved under argon in a mixture of 1800 ml of tetrahydrofuran and 645 ml of 0.067M phosphate buffer of pH value 7. The solution was treated with 19.8 g of copper(II) chloride dihydrate and stirred at room temperature for 16 hours. 1000 ml of ethyl acetate were added to the reaction mixture and it was washed three times with 1500 ml of a mixture of 25% ammonia solution and saturated ammonium chloride solution (1:19) each time. The aqueous wash phases were extracted twice with 1000 ml of ethyl acetate, the organic phases were combined, dried over $MgSO_4$ and freed from solvent. There were obtained 39.7 g of crude 1,2,3,4-tetrahydro-7-methoxy-1-oxo-2-naphthaleneacetaldehyde dimethyl acetal which was processed without purification.

d) For the cleavage of the acetal, 200 ml of a 10% aqueous oxalic acid solution were applied to 1000 g of silica gel and 39.7 g of 1,2,3,4-tetrahydro-7-methoxy-1-oxo-2-naphthaleneacetaldehyde dimethyl acetal were chromatographed on this mixture with methylene chloride as the eluent. There were obtained 28.1 g (88% based on the product from Example 63.b) of 1,2,3,4-tetrahydro-7-methoxy-1-oxo-2-naphthaleneacetaldehyde.

e) N-Acetylethylenediamine (14.5 g) was dissolved in 250 ml of methylene chloride under argon, treated in succession with 250 g of molecular sieve 4 Å and a solution of 28.1 g of 1,2,3,4-tetrahydro-7-methoxy-1-oxo-2-naphthaleneacetaldehyde in 190 ml of methylene chloride and refluxed for 21 hours while stirring. The reaction mixture was cooled, filtered over a Celite ® pad and the filtrate was freed from solvent. The crude product, 35.3 g of brown, amorphous material, was chromatographed on 600 g of silica gel with ethyl acetate as the eluent. There were obtained 29.6 g (81%) of N-[2-(4,5-dihydro-8-methoxy-1H-benzo[g]indol-1-yl)-ethyl]acetamide which was processed without further purification.

f) N-[2-(4,5-Dihydro-8-methoxy-1H-benzo[g]indol-1-yl)-ethyl]acetamide (4.7 g) was treated with 15 ml of phosphorus oxychloride under argon and the mixture was stirred at 50° C. for 30 minutes. The cooled mixture was added to 2000 g of ice-water and treated with 200 ml of 28% sodium hydroxide solution. The mixture was extracted once with 300 ml of methylene chloride and twice with 100 ml of methylene chloride each time, the organic phases were combined, dried with $MgSO_4$ and freed from solvent. 4.2 g of residue were chromatographed on 250 g of aluminium oxide (neutral, III) with methylene chloride as the eluent. 3.8 g of crude product were dissolved in a 20-fold amount of hot ethanol and treated while hot with 1.1 equivalents of a saturated solution of fumaric acid in ethanol. There were obtained 4.7 g (84%) of 5,6,10,11-tetrahydro-2-methoxy-8-methylbenzo[g]pyrazino[1,2-a]indole fumarate (1:1); m.pt.: 175°-177° C. (dec.).

EXAMPLE 64

Trifluoromethanesulphonic acid 5,6,10,11-tetrahydro-8-methyl-benzo[g]pyrazino[1,2-a]indol-3-yl ester (0.4 g), 0.37 g of anhydrous lithium chloride, 85 mg of bis(triphenylphosphine)palladium dichloride, 0.16 g of triphenylphosphine and 0.3 g of tetramethyltin were suspended in 8 ml of dimethylformamide and heated to 120° C. for 3 h. while stirring. The reaction mixture was added to 120 ml of water and extracted with ethyl acetate (1×60 ml, 1×50 ml). The organic phases were washed with 120 ml of saturated sodium chloride solution, combined, dried with MgSO$_4$ and freed from solvent. The residue, 0.5 g of brown oil, was chromatographed on 30 g of silica gel with methylene chloride/methanol mixtures (20:1 to 10:1). There was obtained 0.16 g of crude product which was dissolved in a 20-fold amount of ethanol and treated with 1.1 equivalents of a saturated solution of fumaric acid in ethanol. After concentration to a volume of about 3 ml and addition of 5 ml of ethyl acetate there separated 78 mg (20%) of 5,6,10,11-tetrahydro-3,8-dimethyl-benzo[g]pyrazino[1,2-a]indole fumarate (1:1); m.pt.: 210°–211° C. (dec.).

EXAMPLE 65

Trifluoromethanesulphonic acid 5,6,10,11-tetrahydro-8-methyl-benzo[g]pyrazino[1,2-a]indol-3-yl ester (0.7 g), 0.65 g of anhydrous lithium chloride, 0.15 g of bis(triphenylphosphine)palladium dichloride, 0.29 g of triphenylphosphine and 1.4 g of tri-n-butyl-1-cyclohex-en-1-yl-tin were suspended in 12 ml of dimethylformamide under argon and heated to 120° C. for 3 h. while stirring. The reaction mixture was added to 100 ml of water and extracted twice with 100 ml of ethyl acetate each time. The organic phases were washed with 50 ml of saturated sodium chloride solution, combined, dried with MgSO$_4$ and freed from solvent. The residue, 1.6 g of brown oil, was chromatographed on 50 g of silica gel with methylene chloride/methanol/ammonia mixtures (100:3:0.3 to 100:5:0.5). 0.15 g of 0.65 g of crude product was dissolved in a 25-fold amount of ethanol and treated with 1.1 equivalents of a saturated solution of fumaric acid in ethanol. After the addition of 5 ml of ethyl acetate there separated 40 mg (19%) of 3-cyclohex-1-enyl-5,6,10,11-tetrahydro-8-methyl-benzo[g]pyrazino[1,2-a]indole fumarate (2:3); m.pt.: 181°–183° C. (dec.).

EXAMPLE 66 a) Trifluoromethanesulphonic acid 5,6,10,11-tetrahydro-8-methyl-benzo[g]pyrazino[1,2-a]indol-3-yl ester (2.0 g), 1.85 g of anhydrous lithium chloride, 0.44 g of bis(triphenylphosphine)palladium dichloride, 0.88 g of triphenylphosphine and 3.9 g of tri-n-butyl-2-cyclohex-en-1-yl-tin were suspended in 30 ml of dimethylformamide under argon and heated to 120° C. for 4 h. while stirring. The reaction mixture was cooled and stirred at room temperature overnight with 5 ml of pyridine and 0.6 g of hydrogen fluoride-pyridine complex (60% HF). The reaction mixture was added to 100 ml of 2N sodium hydroxide solution and stirred with 500 ml of diethyl ether for 10 minutes. Subsequently, the mixture was filtered over Celite ®, the aqueous phase was extracted twice with 100 ml of diethyl ether each time and the organic phases were washed in succession with 100 ml of 2N sodium hydroxide solution and 100 ml of saturated sodium chloride solution, combined, dried with MgSO$_4$ and freed from solvent. The residue, 6.8 g of yellow oil, was chromatographed on 60 g of silica gel with methylene chloride and methylene chloride/methanol/ammonia mixtures (30:1:0.1 to 20:1:0.1). There were obtained 1.05 g (64%) of 3-cyclohex-2-enyl-5,6,10,11-tetrahydro-8-methyl-benzo[g]pyrazino[1,2-a]indole as the crude product which was processed without further purification.

b) 3-Cyclohex-2-enyl-5,6,10,11-tetrahydro-8-methyl-benzo[g]pyrazino[1,2-a]indole (1.05 g) was dissolved in 100 ml of methanol and treated with 0.2 ml of methanesulphonic acid. After the addition of 100 mg of tris(triphenylphosphine)-rhodium-(I) chloride the mixture was hydrogenated at room temperature for 24 hours. The mixture was freed from solvent, treated with 100 ml of 10% ammonia solution and extracted three times with 100 ml of methylene chloride each time. The organic phases were combined, dried with MgSO$_4$ and freed from solvent. The residue, 0.95 g of yellow oil, was dissolved in a 20-fold amount of ethanol and treated with 1.1 equivalents of a saturated solution of fumaric acid in ethanol. After concentration to a volume of about 16 ml and addition of 30 ml of ethyl acetate there separated 0.57 g of yellow crystals which were recrystallized from an ethanol/ethyl acetate mixture (1:2). There was obtained 0.39 g (37%) of 3-cyclohexyl-5,6,10,11-tetrahydro-8-methyl-benzo[g]pyrazino[1,2-a]indole fumarate (1:1); m.pt.: 165°–167° C. (dec.).

EXAMPLE 67

Trifluoromethanesulphonic acid 5,6,10,11-tetrahydro-8-methyl-benzo[g]pyrazino[1,2-a]indol-3-yl ester (2.0 g), 1.85 g of anhydrous lithium chloride, 0.44 g of bis(triphenylphosphine)palladium dichloride, 0.88 g of triphenylphosphine and 3.4 ml of tetra-n-butyltin were suspended under argon in 40 ml of dimethylformamide and heated to 120° C. for 6 h. while stirring. The reaction mixture was cooled and stirred at room temperature overnight with 5 ml of pyridine and 0.6 g of hydrogen fluoride-pyridine complex (60% HF). The reaction mixture was added to 100 ml of 2N sodium hydroxide solution and stirred with 500 ml of diethyl ether for 10 minutes. Subsequently, the mixture was filtered over Celite ®, the aqueous phase was extracted twice with 100 ml of diethyl ether each time and the organic phases were washed in succession with 100 ml of 2N sodium hydroxide solution, 100 ml of water and 100 ml of saturated sodium chloride solution, combined, dried with MgSO$_4$ and freed from solvent. The residue, 2.2 g of yellow oil, was chromatographed on 50 g of silica gel with methylene chloride/methanol/ammonia mixtures (30:1:0.1 to 20:1:0.1). There was obtained 0.8 g of crude product which was dissolved in a 20-fold amount of ethanol and treated with 1.1 equivalents of a saturated solution of fumaric acid in ethanol. After concentration to a volume of about 10 ml and addition of 30 ml of ethyl acetate there separated 0.38 g (16%) of 3-butyl-5,6,10,11-tetrahydro-8-methyl-benzo[g]pyrazino[1,2-a]indole fumarate (2:3); m.pt.: 146°–148° C. (dec.).

EXAMPLE 68

3-Cyclohexyl-5,6,10,11-tetrahydro-8-methyl-benzo[g]pyrazino[1,2-a]indole (0.34 g) was dissolved in a mixture of 15 ml of methanol and 1,5 ml of water under argon. The solution was treated portionwise with 0.15 g of sodium borohydride while stirring and stirred at room temperature for 3 hours. Thereafter, the methanol was removed in a vacuum and the residue was stirred with 20 ml of ether and 20 ml of 10% ammonia solution.

The phases were separated and the aqueous phase was extracted twice with 20 ml of ether each time. The organic phases were combined, dried with MgSO₄ and freed from solvent. The crude product, 0.35 g of colourless oil, was dissolved in a 20-fold amount of ethanol and boiled briefly with 1.1 equivalents of a saturated solution of fumaric acid in ethanol. There was obtained 0.11 g (27%) of 3-cyclohexyl-5,6,8,9,10,11-hexahydro-8-methyl-benzo[g]pyrazino[1,2-a]indole fumarate (2:1); m.pt.: 199°-202° C. (dec.).

EXAMPLE 69

3-n-Butyl-5,6,10,11-tetrahydro-8-methyl-benzo[g-]pyrazino[1,2-a]indole (0.47 g) was dissolved in a mixture of 20 ml of methanol and 2 ml of water under argon. The solution was treated portionwise with 0.18 g of sodium borohydride while stirring and stirred at room temperature for 4 hours. Thereafter, the methanol was removed in a vacuum and the residue was stirred with 50 ml of ether and 20 ml of 10% ammonia solution. The phases were separated and the aqueous phase was extracted once with 50 ml of ether. The organic phases were combined, dried with MgSO₄ and freed from solvent. The crude product, 0.47 g of yellowish oil, was dissolved in a 20-fold amount of ethanol and boiled briefly with 1.1 equivalents of a saturated solution of fumaric acid in ethanol. There was obtained 0.11 g (19%) of 3-n-butyl-5,6,8,9,10,11-hexahydro-8-methyl-benzo[g]pyrazino[1,2-a]indole fumarate (2:1); m.pt.: 174°-176° C. (dec.).

EXAMPLE 70

Trifluoromethanesulphonic acid 5,6,10,11-tetrahydro-8-methyl-benzo[g]pyrazino[1,2-a]indol-3-yl-ester (2.0 g), 1.85 g of anhydrous lithium chloride, 0.44 g of bis(triphenylphosphine)palladium dichloride, 0.88 g of triphenylphosphine and 3.5 g of tri-n-butyl-cyclopropyltin were suspended in 25 ml of dimethylformamide under argon and heated to 120° C. for 6 h. while stirring. The reaction mixture was added to 500 ml of water and extracted once with 200 ml of ethyl acetate and twice with 100 ml of ethyl acetate each time. The ethyl acetate extracts were extracted four times with 2N hydrochloric acid (1×100 ml, 3×50 ml), the aqueous phases were combined, made basic with 120 ml of 28% sodium hydroxide solution and extracted three times with 100 ml of methylene chloride each time. The combined methylene chloride extracts were washed twice with 60 ml of saturated potassium fluoride solution each time and once with 500 ml of water. The organic phase was dried with MgSO₄ and freed from solvent. The residue, 1.1 g of brown oil, was chromatographed on 60 g of aluminium oxide (neutral, III) with methylene chloride as the eluent. There was obtained 0.67 g of crude product which was again chromato-graphed on 8 g of silica gel with methylene chloride/methanol mixtures (50:1 to 20:1). The product, 0.14 g of brown oil, was dissolved in a 10-fold amount of ethanol and treated with 1.1 equivalents of a saturated solution of fumaric acid in ethanol. After concentration to a volume of about 1 ml and addition of 3 ml of ethyl acetate there separated 0.11 g of brown crystals which were recrystallized from 4 ml of isopropanol. There were obtained 50 mg (4%) of 3-cyclopropyl-5,6,10,11-tetrahydro-8-methyl-benzo[g]pyrazino[1,2-a]indole fumarate (1:1); m.pt.: 184°-187° C. (dec.).

EXAMPLE A

Tablets of the following composition are produced in the usual manner:

|  | mg/tablet |
| --- | --- |
| Active ingredient | 100 |
| q. lactose | 95 |
| White corn starch | 35 |
| Polyvinylpyrrolidone | 8 |
| Na carboxymethyl starch | 10 |
| Magnesium stearate | 2 |
| Tablet weight | 250 |

EXAMPLE B

Tablets of the following composition are produced in the usual manner:

|  | mg/tablet |
| --- | --- |
| Active ingredient | 200 |
| Powd. lactose | 100 |
| White corn starch | 64 |
| Polyvinylpyrrolidone | 12 |
| Na carboxymethyl starch | 20 |
| Magnesium stearate | 4 |
| Tablet weight | 400 |

EXAMPLE C

Capsules of the following composition are produced:

|  | mg/capsule |
| --- | --- |
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of the formula:

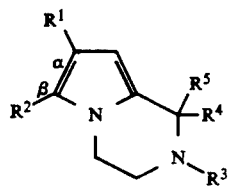

wherein
one of $R^1$ and $R^2$ is aryl and the other is hydrogen, lower alkyl or aryl, or $R^1$ and $R^2$ together with the two carbon atoms denoted by $\alpha$ and $\beta$, is the following group A:

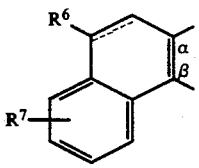

wherein:
R³ is hydrogen or lower alkyl and R⁴ is hydrogen or R³ and R⁴ together are an additional C—N bond;
R⁵ is hydrogen or lower alkyl;
R⁶ is hydrogen or lower alkyl;
R⁷ is hydrogen, halogen, lower alkyl, unsubstituted lower alkoxy, $C_{3-6}$-cycloalkyl, $C_{4-6}$-cycloalkenyl, $C_{3-6}$-cycloalkyloxy, hydroxy, trifluoromethanesulphonyloxy, unsubstituted benzyloxycarbonyloxy, benzyloxyxcarbonyloxy substituted on its phenyl ring with nitro, or substituted lower alkoxy wherein at least one hydrogen atom on the alkyl group is replaced by (i) oxo, (ii) hydroxy, (iii) a 5- or 6-membered unsubstituted saturated heterocycle ring having one nitrogen atom with the remaining ring atoms being carbon, the ring being attached via the nitrogen atom, or (iv) a 5- or 6-membered unsubstituted saturated heterocycle ring having one nitrogen atom and one oxygen atom with the remaining ring atoms being carbon, the ring being attached via the nitrogen atom; and
the ring carbon atom substituted by R⁶ can be saturated or unsaturated;
and pharmaceutically acceptable acid addition salts of the compounds of formula I.

2. The compound according to claim 1, wherein one of R¹ and R² is aryl and the other is hydrogen or aryl, or R¹ and R² together with the two carbon atoms denoted by α and β are group A, and R⁷ is hydrogen, halogen, lower alkyl hydroxy, lower alkoxy or $C_{3-6}$-cycloalkyloxy, wherein aryl is phenyl, phenyl which is mono- or disubstituted by halogen, lower alkoxy, lower alkyl, hydroxy, trifluoromethyl, phenyl-lower-alkoxy or $C_{3-6}$-cycloalkyloxy, or phenyl which is substituted by lower alkylenedioxy.

3. The compound according to claim 1, wherein R¹ and R² together are group A.

4. A compound according to claim 3, wherein R⁷ is $C_{3-6}$-cycloalkyl, $C_{3-6}$-cycloalkyloxy, halogen, lower alkoxy or lower alkyl.

5. The compound according to claim 1, wherein R¹ is hydrogen and R² is aryl.

6. The compound according to claim 1, which is 3,4-dihydro-1-methyl-6-[p-(2-exonorbornyloxy)-phenyl]pyrrolo[1,2-a]pyrazine.

7. The compound according to claim 1, which is 3-cyclopentyloxy-5,6,10,11-tetrahydro-8-methylbenzo[g]pyrazino-[1,2-a]indole.

8. The compound according to claim 1, which is 5,6,10,11-tetrahydro-3-isopropoxy-8-methylbenzo[g]pyrazino[1,2-a]indole.

9. The compound according to claim 1, which is 3-n-butyl-5,6,10,11-tetrahydro-8-methylbenzo[g]pyrazino[1,2-a]indole.

10. The compound according to claim 1, which is 3-cyclohexyl-5,6,10,11-tetrahydro-8-methylbenzo[g]pyrazino[1,2-a]indole.

11. The compound according to claim 1, which is 5,6,10,11-tetrahydro-3,8-dimethylbenzo[g]pyrazino[1,2-a]indole.

12. A compound of the formula:

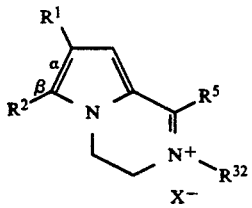

VI wherein
one of R¹ and R² is aryl and the other is hydrogen, lower alkyl or aryl, or R¹ and R² together with the two carbon atoms denoted by α and β, is the following group A:

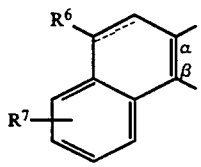

A wherein:
X is halogen;
R³² is lower alkyl;
R⁵ is hydrogen or lower alkyl;
R⁶ is hydrogen or lower alkyl;
R⁷ is hydrogen, halogen, lower alkyl, unsubstituted lower alkoxy, $C_{3-6}$-cycloalkyl, $C_{4-6}$-cycloalkenyl, $C_{3-6}$-cycloalkyloxy, hydroxy, trifluoromethanesulphonyloxy, unsubstituted benzyloxycarbonyloxy, substituted benzyloxycarbonyl wherein a hydrogen atom on the phenyl ring is replaced by a nitro group, or substituted lower alkoxy wherein at least one hydrogen atom on the alkyl group is replaced by (i) oxo, (ii) hydroxy, (iii) a 5- or 6-membered unsubstituted saturated heterocycle ring having one nitrogen atom with the remaining ring atoms being carbon, the ring being attached via the nitrogen atom, or (iv) a 5- or 6-membered unsubstituted saturated heterocycle ring having one nitrogen atom and one oxygen atom with the remaining ring atoms being carbon, the ring being attached via the nitrogen atom; and the ring carbon atom substituted by R⁶ can be saturated or unsaturated.

13. A medicament comprising a compound having the formula:

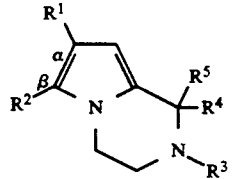

I wherein
one of R¹ and R² is aryl and the other is hydrogen, lower alkyl or aryl, or R¹ and R² together with the two carbon atoms denoted by α and β, is the following group A:

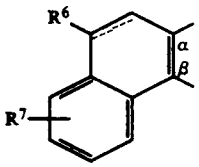

wherein:
R[3] is hydrogen or lower alkyl and R[4] is hydrogen or R[3] and R[4] together are an additional C—N bond;
R[5] is hydrogen or lower alkyl;
R[6] is hydrogen or lower alkyl;
R[7] is hydrogen, halogen, lower alkyl, unsubstituted lower alkoxy, $C_{3-6}$-cycloalkyl, $C_{4-6}$-cycloalkenyl, $C_{3-6}$-cycloalkyloxy, hydroxy, trifluoromethanesulphonyloxy, unsubstituted benzyloxycarbonyloxy, benzyloxycarbonyloxy substituted on its phenyl ring with nitro, or substituted lower alkoxy wherein at least one hydrogen atom on the alkyl group is replaced by (i) oxo, (ii) hydroxy, (iii) a 5- or 6-membered unsubstituted saturated heterocycle ring having one nitrogen atom with the remaining ring atoms being carbon, the ring being attached via the nitrogen atom, or (iv) a 5- or 6-membered unsubstituted saturated heterocycle ring having one nitrogen atom and one oxygen atom with the remaining ring atoms being carbon, the ring being attached via the nitrogen atom; and the ring carbon atom substituted by R[6] can be saturated or unsaturated;

and pharmaceutically acceptable acid addition salts of the compounds of formula I; and a therapeutically inert carrier material.

* * * * *